(12) United States Patent
Ito et al.

(10) Patent No.: US 8,974,830 B2
(45) Date of Patent: Mar. 10, 2015

(54) PARTICLES AND CONTRAST AGENT INCLUDING THE SAME FOR OPTICAL IMAGING

(71) Applicant: Canon Kabushiki Kaisha, Tokyo (JP)

(72) Inventors: Shinzaburo Ito, Kyoto (JP); Kengo Kanazaki, Kyoto (JP); Tatsuki Fukui, Yokohama (JP); Fumiko Tomatsu, Yokohama (JP); Masato Minami, Kawasaki (JP); Tetsuya Yano, Kyoto (JP); Hiroyuki Aoki, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/772,958

(22) Filed: Feb. 21, 2013

(65) Prior Publication Data

US 2013/0243694 A1    Sep. 19, 2013

(30) Foreign Application Priority Data

Feb. 23, 2012    (JP) .................................. 2012-037576

(51) Int. Cl.
*A61K 9/14* (2006.01)
*A61K 49/22* (2006.01)
*A61K 9/16* (2006.01)
*A61K 49/00* (2006.01)

(52) U.S. Cl.
CPC ............. *A61K 49/222* (2013.01); *A61K 9/1647* (2013.01); *A61K 49/0036* (2013.01); *A61K 49/0093* (2013.01)
USPC ........................................................ 424/489

(58) Field of Classification Search
None
See application file for complete search history.

(56) References Cited

U.S. PATENT DOCUMENTS

| 6,498,945 B1 | 12/2002 | Alfheim |
| 2005/0175709 A1 * | 8/2005 | Baty et al. ...................... 424/489 |
| 2008/0095699 A1 * | 4/2008 | Zheng et al. ................. 424/1.11 |
| 2011/0104069 A1 | 5/2011 | Xu |

FOREIGN PATENT DOCUMENTS

WO    WO2009/107859 A2    9/2009

OTHER PUBLICATIONS

Astete et al, Synthesis and characterization of PLGA nanoparticles, J. Biomater. Sci. Polymer Edn, 2006, 17(3), 247-289.*
Hagemeyer et al, Single-chain antibodies as diagnostic tools and therapeutic agents, Thromb. Haemost., 2009, 101, 1012-1019.*
Vishal Saxena et al., Enhanced photo-stability, thermal-stability and aqueous-stability of indocyanine green in polymeric nanoparticulate systems, Journal of Photochemistry and Photobiology B: Biology, 74(2004) 29-38.
Hiroyuki Aoki et al, Development of Polymer Nano-Particle with Near-Infrared Absorption as Contrast Agent for Photoacoustic Tomography, Kyoto University, Kyoto Japan, 2004.

* cited by examiner

*Primary Examiner* — Paul Dickinson
(74) *Attorney, Agent, or Firm* — Canon U.S.A. Inc., IP Division

(57) ABSTRACT

A particle includes a copolymer of lactic acid and glycolic acid, and at least one compound selected from silicon naphthalocyanine and derivatives of silicon naphthalocyanine, in which the particle has a particle size of 10 nm or more and less than 1000 nm.

11 Claims, 8 Drawing Sheets

FIG. 7A
FIG. 7B
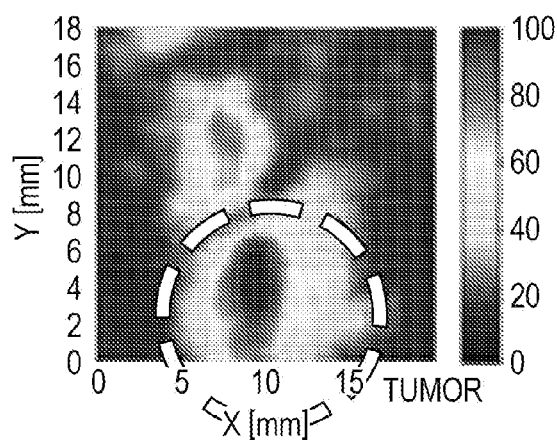
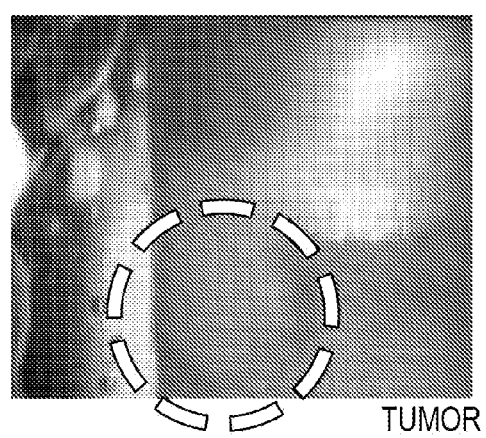
FIG. 7C
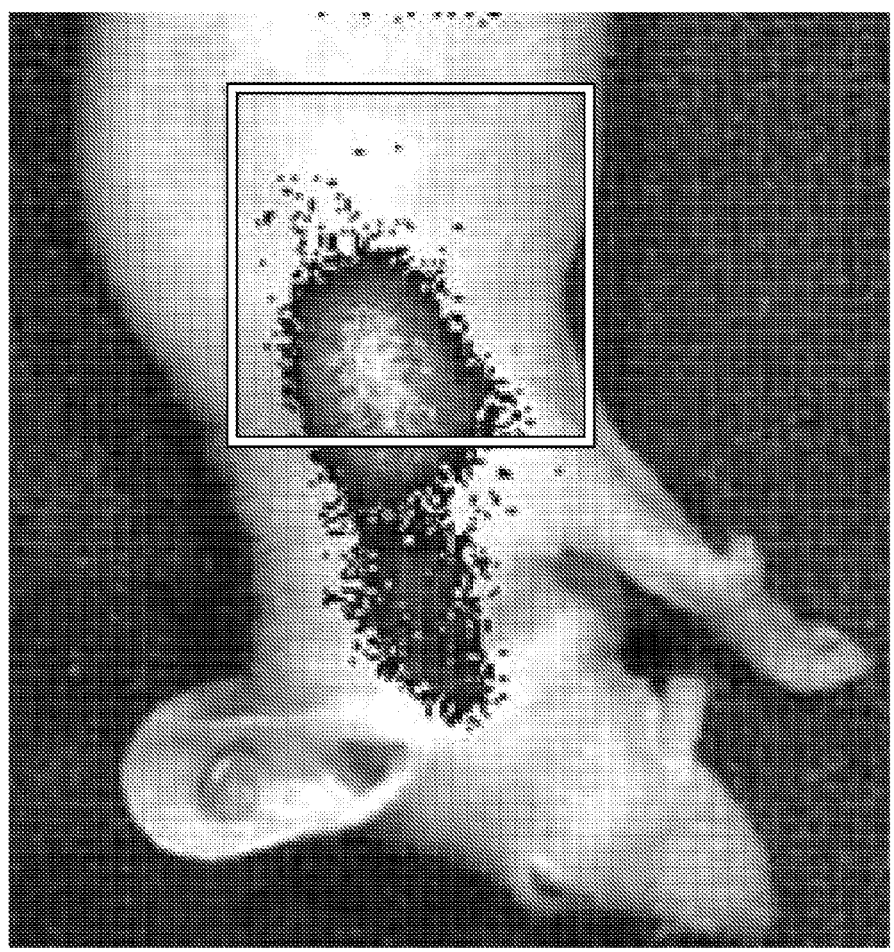

PARTICLES AND CONTRAST AGENT INCLUDING THE SAME FOR OPTICAL IMAGING

BACKGROUND OF THE INVENTION

1. Field of the Invention

The present invention relates to particles and a contrast agent including the particles for optical imaging.

2. Description of the Related Art

A photoacoustic tomography (hereinafter, also referred to as "PAT") apparatus is known as one of apparatuses for visualizing in-vivo information. In the measurement using a PAT apparatus, a tomographic image can be obtained by measuring the intensity and the time of generation of a photoacoustic signal emitted from a substance (optical absorber) that absorbs light in an object to be measured when the object is irradiated with light, and computing a distribution of the substance in the object.

A substance that absorbs light and emits an acoustic wave in a living body may be used as an optical absorber. For example, a blood vessel or a malignancy in the human body may be used as an optical absorber. In addition, for example, dyes that absorb light in the near-infrared wavelength region may be administered into the body and used as contrast agents. Light in the near-infrared wavelength region has little influence on the human body when the human body is irradiated with the light and has a high permeability to a living body. Thus, dyes that absorb the light may be suitably used as contrast agents for use in PAT apparatuses and fluorescence apparatuses.

To accumulate dyes that absorb light in the near-infrared wavelength region at measurement sites, such dyes are often entrapped in particles and used as contrast agents. Journal of Photochemistry and Photobiology B: Biology, 74 (2004), 29-38 (hereinafter, referred to as "Non-Patent Document 1") discloses particles of a copolymer of lactic acid and glycolic acid (poly(lactide-co-glycolide), hereinafter, also referred to as "PLGA"), the particles containing indocyanine green (hereinafter, also referred to as "ICG") and being prepared by an emulsion solvent diffusion method with polyvinyl alcohol (PVA) as a surfactant.

In the case of measurement with a PAT apparatus using a contrast agent entrapping a dye in particles, the dye in the contrast agent may be entrapped in high density. This is because a larger amount of the dye entrapped in the particles results in a higher molar extinction coefficient per unit particle and a higher photoacoustic signal.

For the ICG-containing particles disclosed in Non-Patent Document 1, the dye may leak from the particles in serum. This may be because ICG has a hydrophilic structure and a hydrophobic structure and is surface active. That is, in the ICG-containing particles disclosed in Non-Patent Document 1, ICG is more abundant on surfaces of the particles than in hydrophobic core portions of the particles. When ICG is mixed with serum, ICG present on the particle surfaces may interact with proteins in the serum to leak outside the particles.

SUMMARY OF THE INVENTION

The present invention has been accomplished in light of the foregoing problems. The present invention provides particles configured to inhibit leakage of a dye entrapped in the particles.

According to aspects of the present invention, a particle includes a copolymer of lactic acid and glycolic acid, and at least one compound selected from silicon naphthalocyanine and derivatives thereof, the particle having a particle size of 10 nm or more and less than 1000 nm.

In the particle according to aspects of the present invention, silicon naphthalocyanine or its derivative, which is a hydrophobic dye, is used, thus resulting in a reduction in the leakage of the dye to the outside the particles. PLGA is used as a component of the particle, thus resulting in high tumor accumulation.

Further features of the present invention will become apparent from the following description of exemplary embodiments with reference to the attached drawings.

BRIEF DESCRIPTION OF THE DRAWINGS

FIGS. 7A, 7B, and 7C are the results of measurements of photoacoustic imaging and fluorescence imaging of a mouse to which particles according to an example of the present invention is administered.

DESCRIPTION OF THE EMBODIMENTS

While embodiments of the present invention will be described below, the present invention is not limited to these embodiments.

A particle according to this embodiment contains a copolymer (PLGA) of lactic acid and glycolic acid, and at least one compound selected from silicon naphthalocyanine and derivatives thereof, the particle having a particle size of 10 nm or more and less than 1000 nm.

The particle according to the embodiment of the present invention contains hydrophobic PLGA and silicon naphthalocyanine or its derivative having a hydrophobic naphthalocyanine skeleton. Thus, leakage outside the particle is reduced, compared with the case of using ICG having a hydrophilic structure. As a result, the particle according to this embodiment has a high molar extinction coefficient per particle and thus may be used as a contrast agent that provides a large photoacoustic signal. As described below, the use of PLGA as a component of the particle increases tumor accumulation.

A single type silicon naphthalocyanine or its derivative may be contained in the particle according to this embodiment. Alternatively, two or more types of compounds selected from silicon naphthalocyanine and derivatives thereof may be contained in the particle.

The particles according to this embodiment may have a capture molecule that binds specifically to a target site.

Example of Particle

Figure 1:
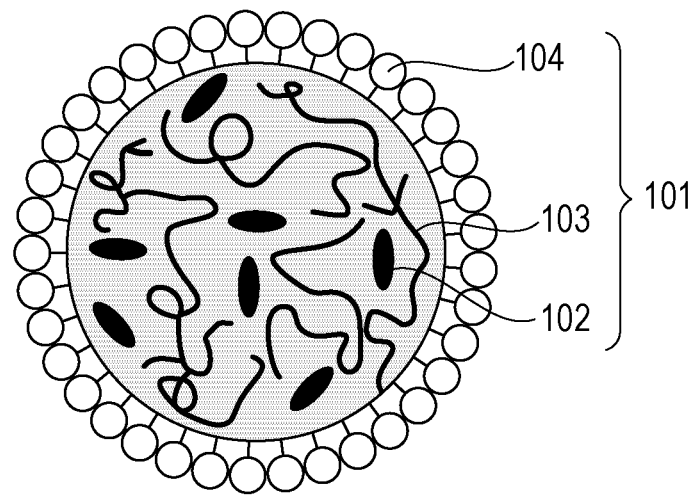
FIG. 1 is a schematic diagram of a structure of a particle according to an embodiment of the present invention.

An example of the particle according to this embodiment will be described below with reference to FIG. 1. A particle 101 according to this embodiment contains silicon naphthalocyanine or its derivative 102; and PLGA 103. Furthermore, the particle 101 includes a surfactant 104 on a surface of the particle 101. The particles 101 are not easily aggregated in water by the use of the surfactant 104.

Another Example of Particle

Figure 2:
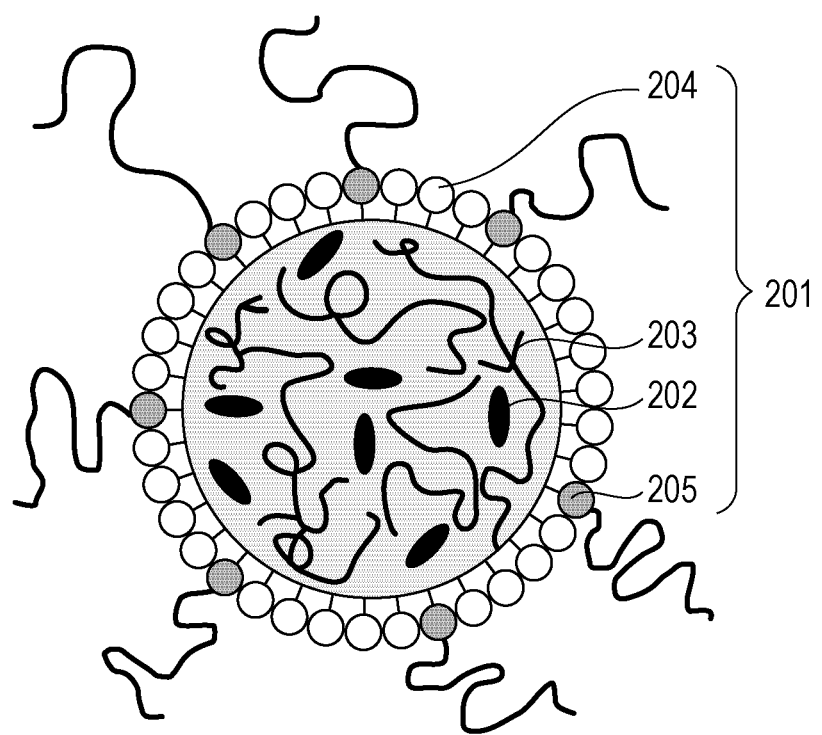
FIG. 2 is a schematic diagram of a structure of a particle according to another embodiment of the present invention.

As illustrated in FIG. 2, another example of the particle according to this embodiment is a particle 201 that contains silicon naphthalocyanine or its derivative 202, and PLGA 203. Furthermore, the particle 201 includes a first surfactant 204 and a second surfactant 205 on a surface of the particle 201. The particle 201 is not easily aggregated in water by the use of the first surfactant 204. In the case where the second surfactant 205 is composed of a compound having a functional group, such as an amino group or a maleimide group, at an end, a protein, such as an antibody, may bind to the surface of the particle 201 through an amide bond or a bond formed by a coupling reaction of a maleimide group with a thiol group.

Particle Size

The particle according to this embodiment has a particle size of 10 nm or more and less than 1000 nm. In the case where the particle according to this embodiment has a particle size of less than 1000 nm, a larger number of particles can be accumulated in a tumor site than in normal sites in a living body by the enhanced permeability and retention (EPR) effect. The accumulated particles are detected by various image forming modalities, such as fluorescent and photoacoustic methods, to specifically form an image of the tumor site. The particle size of the particle is preferably 500 nm or less and more preferably 200 nm or less. The reason for this is that when the particle according to this embodiment has a particle size of 200 nm or less, the particles are probably less likely to be taken up by macrophages in blood, thereby increasing retention in blood.

In this embodiment, the particle size may be determined by measuring a rheological diameter using a dynamic light scattering (DLS) method with, for example, a dynamic light scattering spectrophotometer (DLS-8000, manufactured by Otsuka Electronics Co., Ltd).

Silicon Naphthalocyanine or its Derivative

In this embodiment, silicon naphthalocyanine or its derivative is, for example, a compound represented by chemical formula 3.

For example, silicon 2,3-naphthalocyanine bis(trihexylsilyloxide) (hereinafter, also referred to as "compound 1") represented by chemical formula 1, silicon 2,3-naphthalocyanine dihydroxide represented by chemical formula 2, silicon 2,3-naphthalocyanine dioctyloxide, silicon 2,3-naphthalocyanine dichloride, or bis(di-isobutyl octadecylsiloxy)silicon 2,3-naphthalocyanine (isoBOSINC) may be used. In particular, silicon 2,3-naphthalocyanine bis(trihexylsilyloxide) represented by chemical formula 1 may be used.

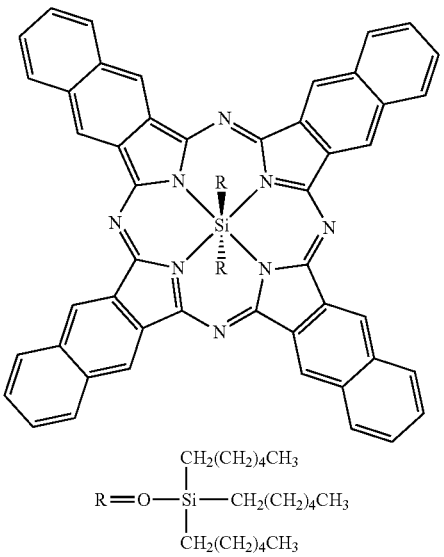

(Chemical formula 1)

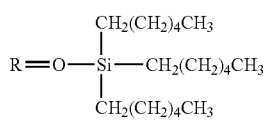

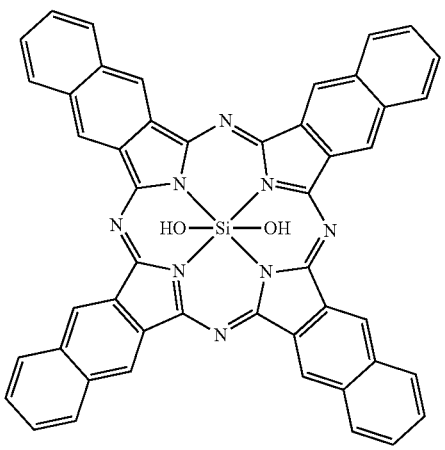

(Chemical formula 2)

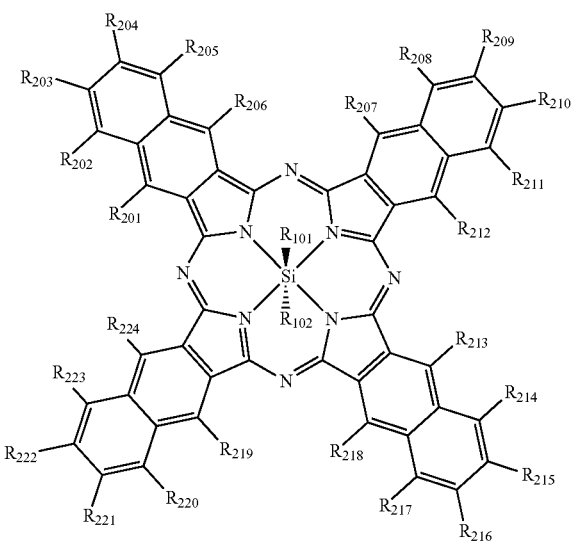

(Chemical formula 3)

wherein in chemical formula 3, $R_{201}$ to $R_{224}$ are each independently selected from a hydrogen atom, a halogen atom, an acetoxy group, an amino group, a nitro group, a cyano group, a substituted or unsubstituted alkyl group having 1 to 18 carbon atoms, and a substituted or unsubstituted aromatic group, and the substituents of the hydrocarbon group and the aromatic group each represent a halogen atom, an acetoxy group, an amino group, a nitro group, a cyano group, or an alkyl group having 1 to 18 carbon atoms; $R_{101}$ and $R_{202}$ are each independently selected from —OH, —$OR_{11}$, —$OCOR_{12}$, —$OSi(—R_{13})(—R_{14})(—R_{15})$, a halogen atom, an acetoxy group, an amino group, a nitro group, a cyano group, a substituted or unsubstituted alkyl group having 1 to 18 carbon atoms, and a substituted or unsubstituted aromatic group, and the substituents of the hydrocarbon group and the aromatic group each represent a halogen atom, an acetoxy group, an amino group, a nitro group, a cyano group, or an alkyl group having 1 to 18 carbon atoms; and $R_{11}$ to $R_{15}$ are each independently selected from a hydrogen atom, a halogen atom, an acetoxy group, an amino group, a nitro group, a cyano group, a substituted or unsubstituted alkyl group having 1 to 18 carbon atoms, and a substituted or unsubstituted aromatic group, and the substituents of the hydrocarbon group and the aromatic group each represent a halogen atom, an acetoxy group, an amino group, a nitro group, a cyano group, or an alkyl group having 1 to 18 carbon atoms.

In this embodiment, silicon naphthalocyanine or its derivative may absorb light in the near-infrared wavelength region ranging from 600 nm to 900 nm, the light having good penetration through a living body. The reason for this is that in the case where the particles according to this embodiment is administered to a living body and where the positions of the particles are detected with a fluorescent imaging apparatus or photoacoustic imaging apparatus, light in the near-infrared wavelength region can be selected as light used for the apparatus because the light is safe when the living body is irradiated with the light and because the light has relatively high penetration through the living body.

Copolymer of Lactic Acid and Glycolic Acid (PLGA)

The copolymer (PLGA) of lactic acid and glycolic acid used in the particle according to this embodiment is a polymer material formed into a core that forms a particulate shape. PLGA is susceptible to hydrolysis. Thus, when PLGA has become unnecessary, it is speculated that PLGA is less likely to accumulate in vivo and is eliminated from the body. PLGA used in this embodiment preferably has an average molecular weight of 2,000 or more and 1,000,000 or less, more preferably 10,000 or more and 600,000 or less, and particularly preferably 15,000 or more and 25,000 or less. PLGA having an average molecular weight of 20,000 is most preferred. For PLGA, the copolymerization ratio of lactic acid to glycolic acid is preferably in the range of 25:75 to 75:25. For example, PLGA in which the copolymerization ratio of lactic acid: glycolic acid is 25:75, 50:50, or 75:25 may be used. PLGA in which the copolymerization ratio of lactic acid:glycolic acid is 50:50 is most preferred. As lactic acid used for PLGA in this embodiment, the D- and L-forms of lactic acid and racemic lactic acid may be used.

Surfactant

The surfactants (the surfactant 104 illustrated in FIG. 1, the first surfactant 204 and the second surfactant 205 illustrated in FIG. 2) in this embodiment are not particularly limited. As described below, any surfactant capable of forming an emulsion in the process of preparing particles may be used. Examples of a surfactant that may be used include nonionic surfactants, anionic surfactants, cationic surfactants, polymeric surfactants, and phospholipids. These surfactants may be used separately or in combination.

Examples of the nonionic surfactant include polyoxyethylene sorbitan fatty acid esters, such as a compound represented by chemical formula 4, Brij (registered trademark) 35, Brij (registered trademark) 58, Brij (registered trademark) 76, Brij (registered trademark) 98, Triton (registered trademark) X-100, Triton (registered trademark) X-114, Triton (registered trademark) X-305, Triton (registered trademark) N-101, Nonidet (registered trademark) P-40, IGEPAL (registered trademark) CO530, IGEPAL (registered trademark) CO630, IGEPAL (registered trademark) CO720, and IGEPAL (registered trademark) CO730.

(Chemical formula 4)

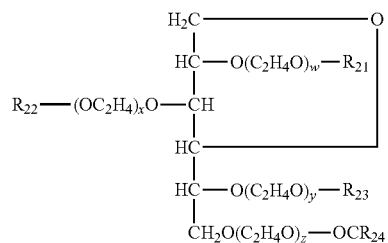

wherein in chemical formula 4, $R_{21}$ to $R_{24}$ are each independently selected from —H and —OCR', R' represents a saturated or unsaturated alkyl group having 1 to 18 carbon atoms; and w, x, y, and z each represent a value such that the sum total of w, x, y, and z is an integer of 10 to 30. An example of chemical formula 4 is the case where w, x, y, and z each independently represent an integer of 1 to 10, provided that the sum total of w, x, y, and z is an integer of 10 to 30.

Examples of polyoxyethylene sorbitan fatty acid esters represented by chemical formula 4 include Tween (registered trademark) 20, Tween (registered trademark) 40, Tween (registered trademark) 60, Tween (registered trademark) 80, and Tween (registered trademark) 85.

Examples of the anionic surfactant include sodium dodecyl sulfate; dodecylbenzene sulfonate, decylbenzene sulfonate, undecylbenzene sulfonate, tridecylbenzene sulfonate, and nonylbenzene sulfonate; and sodium, potassium, and ammonium salts thereof.

Examples of the cationic surfactant include cetyltrimethylammonium bromide, hexadecylpyridinium chloride, dodecyltrimethylammonium chloride, and hexadecyltrimethylammonium chloride.

Examples of the polymeric surfactant include polyvinyl alcohol, polyoxyethylene-polyoxypropylene glycol, and gelatin. Examples of commercially available polyoxyethylene-polyoxypropylene glycol include Pluronic F68 (manufactured by BASF SE) and Pluronic F127 (manufactured by BASF SE).

The phospholipid may be a phosphatidyl phospholipid having any functional group selected from a hydroxy group, a methoxy group, an amino group, a carboxy group, an N-hydroxysuccinimide group, and a maleimide group. The phospholipid used as the surfactant may contain a polyethylene glycol (PEG) chain.

Examples of the phospholipid used as a surfactant which has a functional group selected from a hydroxy group, a methoxy group, an amino group, an N-hydroxysuccinimide group, and a maleimide group and which contains a PEG chain include 1,2-distearoyl-sn-glycero-3-phosphoethanolamine-N—[poly(ethylene glycol)] (DSPE-PEG-OH) represented by chemical formula 5, poly(oxy-1,2-ethanediyl) represented by chemical formula 6, α-[7-hydroxy-7-oxido-13-oxo-10-[(1-oxooctadecyl)oxy]-6,8,12-trioxa-3-aza-7-phosphatriacont-1-yl]-ω-methoxy-(DSPE-PEG-OMe), N-(aminopropyl polyethyleneglycol)-carbamyl distearoylphosphatidyl-ethanolamine (DSPE-PEG-NH$_2$) represented by chemical formula 7,3-(N-succinimidyloxyglutaryl)aminopropyl polyethyleneglycol-carbamyl distearoylphosphatidyl-ethanolamine (DSPE-PEG-NHS) represented by chemical formula 8, and N-(3-maleimide-1-oxopropyl)aminopropyl polyethyleneglycol-carbamyl distearoylphosphatidyl-ethanolamine (DSPE-PEG-MAL) represented by chemical formula 9. In each of the compounds represented by chemical formulae 5 to 9, n represents an integer of 5 or more and 500 or less.

(Chemical formula 5)

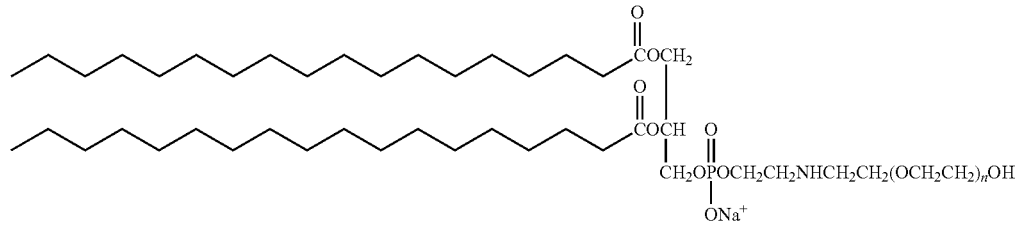

(Chemical formula 6)

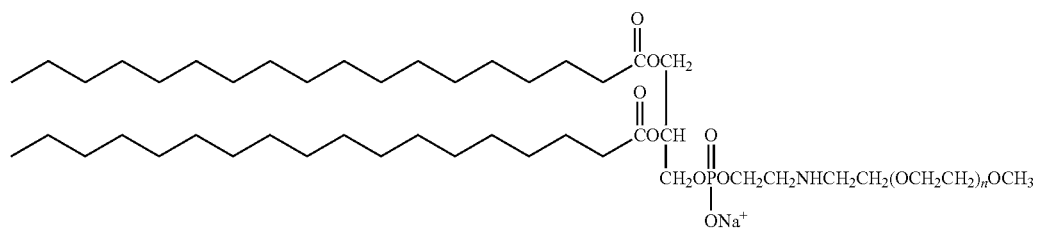

(Chemical formula 7)

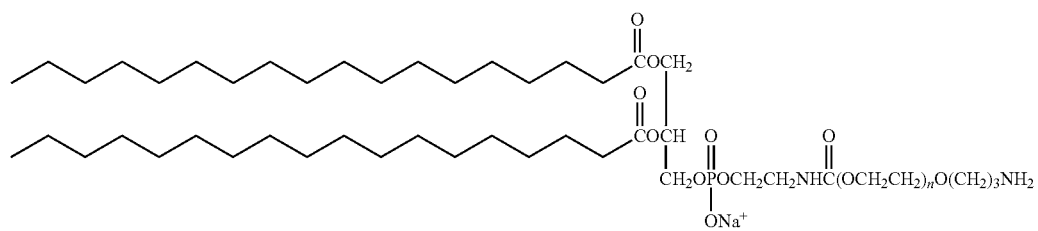

(Chemical formula 8)

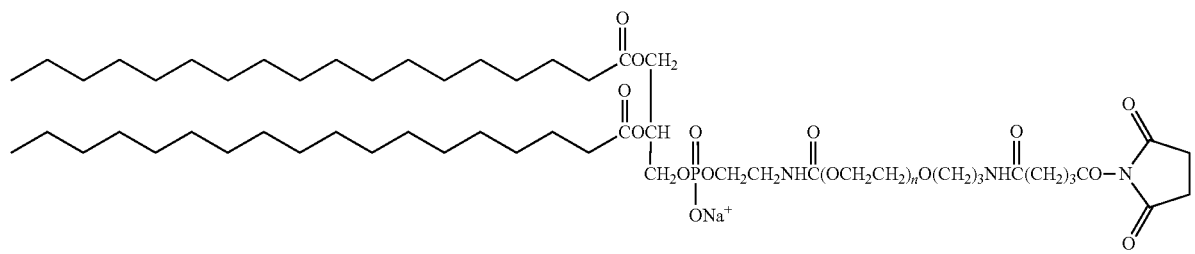

(Chemical formula 9)

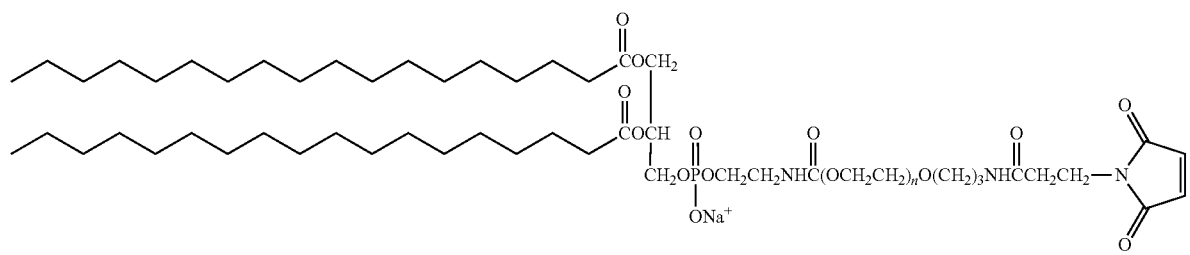

Capture Molecule

A capture molecule in this embodiment is, for example, a substance that binds specifically to a target site, such as a tumor, or a substance that binds specifically to a substance present around a target site. The capture molecule may be freely selected from biomolecules and chemical substances, such as pharmaceuticals. Specific examples thereof include antibodies, antibody fragments, enzymes, biologically active peptides, glycopeptides, sugar chains, lipids, and molecule-recognizing compounds. The antibody may be a single-chain antibody. A specific example of the single-chain antibody is one represented by SEQ ID NO. 2. These substances may be used separately or in combination. According to this embodiment, the use of the particles to which the capture molecule is chemically bonded enables the specific detection of a target site and the tracing of the dynamics, localization, efficacy of medicine, metabolism, and so forth of the target substance.

Contrast Agent for Optical Imaging

A contrast agent for optical imaging according to this embodiment includes the particles according to this embodiment and a dispersion medium, the particles being dispersed in the dispersion medium. The contrast agent for optical imaging according to this embodiment may contain a pharmacologically acceptable additive in addition to the particles according to this embodiment, as needed.

Here, the dispersion medium is composed of a liquid substance used to disperse the particles according to this embodiment. Examples thereof include physiological saline and distilled water for injection. In the case of the contrast agent for optical imaging according to this embodiment, the particles according to this embodiment may be dispersed in the dispersion medium in advance. Alternatively, the particles according to this embodiment and the dispersion medium may be prepared as a kit, and the particles may be dispersed in the dispersion medium prior to the administration of the contrast agent into the body.

In this embodiment, "optical imaging" refers to imaging by irradiation with light. Specifically, the silicon naphthalocyanine or its derivative in the contrast agent for optical imaging according to this embodiment is irradiated with light to emit, for example, an acoustic wave or fluorescence. The detection of the emitted acoustic wave enables photoacoustic imaging. The detection of the emitted fluorescence enables fluorescence imaging. Photoacoustic imaging is a concept including photoacoustic tomography.

In the contrast agent for optical imaging according to this embodiment, a larger number of the particles can be accumulated in a tumor site than in normal sites in a living body by the enhanced permeability and retention (EPR) effect when the contrast agent is administered into the body. Thus, after the particles are administered into the body, in the case where the body is irradiated with light and where an acoustic wave or fluorescence emitted from the body is detected, the intensity of an acoustic wave or fluorescence emitted from the tumor site can be increased, compared with the intensity of acoustic waves or fluorescence emitted from the normal sites. Hence, the particles according to this embodiment may be used as a contrast agent for optical imaging, the contrast agent being capable of specifically detecting a tumor site.

Method for Producing Particle

Figure 3:
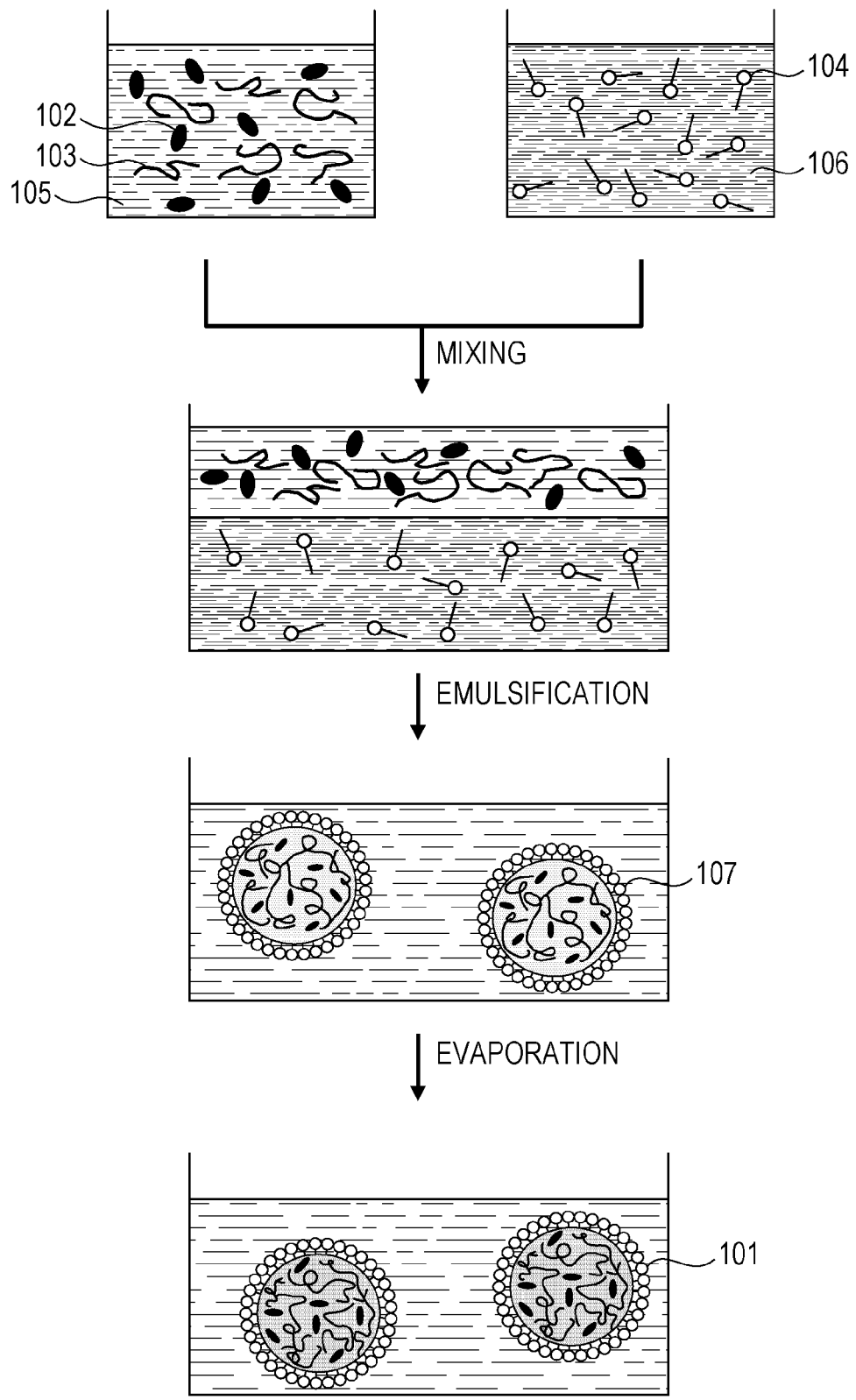
FIG. 3 illustrates an example of steps of producing a particle according to an embodiment of the present invention.

An example of a method for producing the particles according to this embodiment is, but not limited to, a nanoemulsion method. A method for producing the particles by the nanoemulsion method will be described with reference to FIG. 3. FIG. 3 illustrates an example of steps of producing the particles 101 illustrated in FIG. 1 by the nanoemulsion method. Specifically, an aqueous dispersion of the particles 101 may be produced by the following steps (A) to (C):

(A) a step of adding a first liquid 105 to a second liquid 106 to prepare a liquid mixture, the first liquid 105 being prepared by dissolving the silicon naphthalocyanine or its derivative 102 and the PLGA 103 in an organic solvent, and the second liquid 106 being an aqueous solution of the surfactant 104 dissolved therein;

(B) a step of emulsifying the liquid mixture prepared in the step (A) to form an oil-in-water (hereinafter, also referred to as "O/W") emulsion 107; and (C) a step of evaporating the organic solvent contained in the first liquid 105 from dispersoids in the emulsion 107 prepared in the step (B).

Note that the method may include a step other than the steps (A) to (C).

Figure 4:
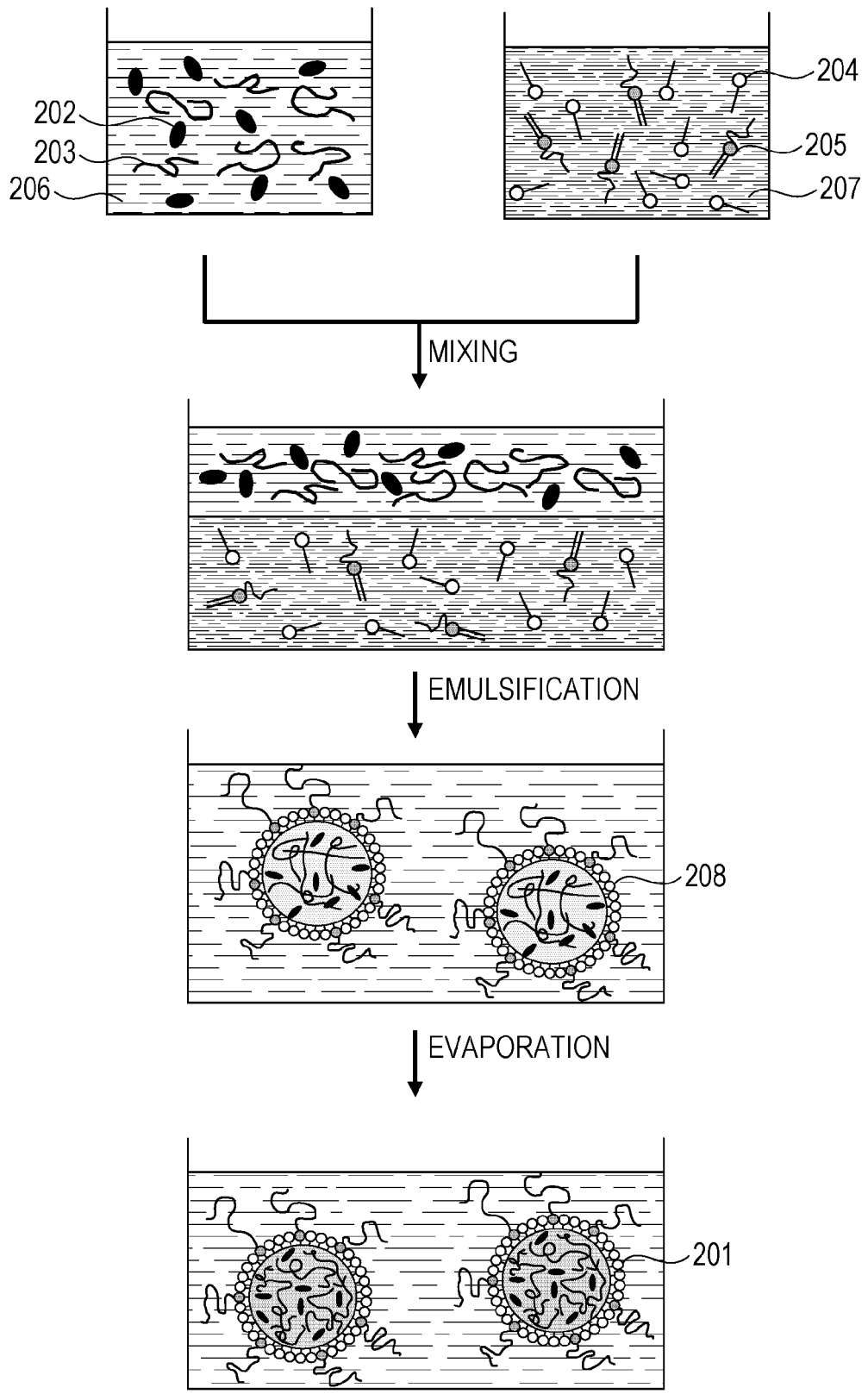
FIG. 4 illustrates an example of steps of producing a particle according to another embodiment of the present invention.

FIG. 4 illustrates an example of a process of producing the particle 201 including two types of surfactants as illustrated in FIG. 2. Specifically, an aqueous dispersion of the particles 201 may be prepared through steps (D) to (F) described below. Note that a particle including three or more types of surfactants may be produced by the same process.

(D) A step of adding a first liquid 206 to a second liquid 207 to prepare a liquid mixture, the first liquid 206 being prepared by dissolving the silicon naphthalocyanine or its derivative 202 and the PLGA 203 in an organic solvent, and the second liquid 207 being an aqueous solution of the first surfactant 204 and the second surfactant 205 dissolved therein.

(E) A step of emulsifying the liquid mixture prepared in step (D) to form an O/W emulsion 208.

(F) A step of evaporating the organic solvent contained in the first liquid 206 from dispersoids in the emulsion 208 prepared in the step (E).

First Liquid

Any organic solvent may be used as a solvent for the first liquid used in the nanoemulsion method as long as the organic solvent is insoluble or has a low degree of solubility in water, and can dissolve silicon naphthalocyanine or its derivative and PLGA. A volatile organic solvent may be used.

Examples of such an organic solvent that may be used include, but are not limited to, halogenated hydrocarbons, such as dichloromethane, chloroform, chloroethane, dichloroethane, trichloroethane, and carbon tetrachloride; ethers, such as ethyl ether and isobutyl ether; esters, such as ethyl acetate and butyl acetate; and aromatic hydrocarbons, such as benzene, toluene, and xylene. These organic solvents may be used separately or in combination as a mixture of two or more of these solvents in appropriate ratios.

The concentration of silicon naphthalocyanine or its derivative in the first liquid may be in the range of 0.0005 to 100 mg/mL.

The concentration of PLGA in the first liquid may be 0.05 or more and 100 mg/mL or less.

The ratio by weight of silicon naphthalocyanine or its derivative to PLGA in the first liquid may be 1:1 or more and 1:100 or less.

Second Liquid

The second liquid used in the nanoemulsion method is an aqueous solution of the surfactant 104 or the first surfactant 204 and the second surfactant 205 dissolved therein. In the case where the second liquid contains the surfactant 104 or the first surfactant 204 and the second surfactant 205 in advance, when the second liquid is mixed with the first liquid, a stable emulsion is formed. In this embodiment, it is good as long as the surfactant 104 or the first surfactant 204 and the second surfactant 205 are contained a dispersion prepared by mixing the first liquid with the second liquid. The surfactant 104 or the first surfactant 204 and the second surfactant 205 are not necessarily dissolved in the second liquid in advance.

The concentration of the surfactant 104 or the first surfactant 204 and the second surfactant 205 in the second liquid varies depending on the type of surfactant used and the mixing ratio of the surfactant to the first liquid. For example, in the case where a nonionic surfactant, an anionic surfactant, a cationic surfactant, or a polymeric surfactant is used, the concentration of the surfactant in the second liquid may be in the range of 0.1 mg/mL to 100 mg/mL. For example, in the case where a phospholipid containing a PEG chain is used as a surfactant, the concentration of the surfactant in the second liquid may be in the range of 0.001 mg/mL to 100 mg/mL.

In the case where a nonionic surfactant, an anionic surfactant, a cationic surfactant, or a polymeric surfactant is used as the first surfactant 204 and where a phospholipid containing a PEG chain is used as the second surfactant 205, the molar ratio of the first surfactant 204 to the second surfactant 205 may be 100:1 or more and 1:1 or less. In the case where the molar ratio of the second surfactant 205 is 1:1 or less, particles may be easily formed. In the case where the molar ratio of the second surfactant 205 is 100:1 or more, when the capture molecule is immobilized, a large number of the capture molecules may be immobilized.

Emulsion

The emulsion prepared by the nanoemulsion method may have any physical properties as long as the advantages of embodiments of the present invention are not impaired. The emulsion may have a single-peak particle size distribution and an average particle size of 1000 nm or less.

Such an emulsion may be prepared by a known emulsification method, for example, an intermittent shaking method, a stirring method using a mixer, such as a propeller stirrer or a turbine stirrer, a colloid mill method, a homogenizer method, or an ultrasonic irradiation method. These methods may be employed separately or in combination. The emulsion may be prepared by single-step emulsification or multistep emulsification. The emulsification method is not limited to these methods as long as the advantages of embodiments of the present invention are not impaired.

The emulsion is an O/W emulsion prepared by the addition of the first liquid to the second liquid. Here, the mixing of the first liquid and the second liquid indicates that the first liquid and the second liquid are in contact with each other without being spatially separated. The first liquid and the second liquid are not necessarily miscible with each other.

The ratio of the first liquid to the second liquid in the liquid mixture is not particularly limited as long as an O/W emulsion can be formed. The first liquid and the second liquid may be mixed together in such a manner that the ratio by weight of the first liquid to the second liquid is 1:2 or more and 1:1000 or less.

Evaporation

Evaporation in the nanoemulsion method indicates an operation of removing the organic solvent contained in the first liquid from the dispersoids of the emulsion. In other words, the evaporation in the nanoemulsion method indicates that the organic solvent is removed from the dispersoids including silicon naphthalocyanine or its derivative, PLGA, and the organic solvent.

The evaporation may be performed by any known method. Examples of the method include a method in which the organic solvent is removed by heating; and a method in which the organic solvent is removed with a pressure-reducing apparatus, such as an evaporator. In the case of removing the organic solvent by heating, the temperature of heating is not particularly limited as long as the O/W emulsion can be maintained. The temperature of heating may be 0° C. or higher and 80° C. or lower. The evaporation is not limited to the foregoing methods as long as the advantages of embodiments of the present invention are not impaired.

Immobilization of Capture Molecule

Depending on the type of capture molecule, any known method may be employed to immobilize a capture molecule on the particle according to this embodiment. An example of the method is a method in which a functional group in the first surfactant 204 or the second surfactant 205 is allowed to react with a functional group of the capture molecule to form a chemical bond.

For example, in the case where the first surfactant 204 or the second surfactant 205 is a phosphatidyl phospholipid having an N-hydroxysuccinimide group, the N-hydroxysuccinimide group may be allowed to react with a capture molecule having an amino group to immobilize the capture molecule on the particle. After the immobilization of the capture molecule, an unreacted N-hydroxysuccinimide group of the surfactant may be inactivated by reaction with, for example, glycine, ethanolamine, or either oligoethylene glycol or polyethylene glycol having an amino group at an end.

In the case where the first surfactant 204 or the second surfactant 205 is a phosphatidyl phospholipid having a maleimide group, the maleimide group may be allowed to react with a capture molecule having a thiol group to immobilize the capture molecule on the particle. After the immobilization of the capture molecule, an unreacted maleimide group of the surfactant may be inactivated by reaction with, for example, L-cysteine, mercaptoethanol, or either oligoethylene glycol or polyethylene glycol having a thiol group at an end.

In the case where the first surfactant 204 or the second surfactant 205 is a phosphatidyl phospholipid having an amino group, the amino group may be allowed to react with an amino group of a capture molecule using glutaraldehyde to immobilize the capture molecule on the particle. After the immobilization of the capture molecule, an unreacted amino group may be inactivated by reaction with, for example, ethanolamine or either oligoethylene glycol or polyethylene glycol having an amino group at an end. Alternatively, an amino group of the surfactant may be replaced with an N-hydroxysuccinimide group or a maleimide group to immobilize the capture molecule.

Imaging Method

A method for detecting the particles according to this embodiment with a PAT apparatus after the particles are administered into a living body will be described below. While the method for detecting the particles according to this embodiment includes steps described below, an imaging method according to this embodiment may further contain a step other than the steps described below.

(a) A step of administering the particles according to this embodiment.

(b) A step of irradiating the body with light and detecting a photoacoustic signal emitted from the particles, present in the body, according to this embodiment.

In the step (a), the method for administering the particles according to this embodiment into the body is not particularly limited. A method, for example, oral administration or injection, may be employed.

In the step (b), an apparatus configured to generate light with which a living body is irradiated, and an apparatus configured to detect an acoustic wave emitted from the particle according to this embodiment are not particularly limited. As the apparatus configured to generate light, for example, a titanium-sapphire laser (LT-2211-PC, manufactured by Lotis Ltd.) may be used. The apparatus configured to detect an acoustic wave is not particularly limited. For example, an ultrasonic probe may be used. In the step (b), light with which the body is irradiated may be near-infrared light having a wavelength of 600 nm to 900 nm, the light being safe when the living body is irradiated with the light, and the light having high penetration through the body. The apparatus configured to generate light and the apparatus configured to detect an acoustic signal are not particularly limited, and various apparatuses may be used.

By employing the imaging method using the particles according to this embodiment, a site, such as a tumor, can be imaged through the steps (a) and (b).

A method for detecting the particles according to this embodiment, the particles being administered into a living body, with a fluorescence imaging apparatus will be described below. The method for detecting the particles according to this embodiment includes the following steps:
(c) a step of administering the particles according to this embodiment; and
(d) a step of irradiating the body with light and detecting fluorescence emitted from the particles, present in the body, according to this embodiment.

In the step (c), a method for administering the particles according to this embodiment into the body is not particularly limited. A method, for example, oral administration or injection, may be employed.

In the step (d), an apparatus configured to generate light with which a living body is irradiated, and an apparatus configured to detect fluorescence emitted from the particles according to this embodiment are not particularly limited.

In the case where capture molecule-containing particles are used in a living body, various target sites can be specifically detected by appropriately selecting the capture molecule. For example, the use of a substance as a capture molecule that binds specifically to a tumor enables specific detection of the tumor. In the case where a substance that binds specifically to a biological substance, for example, protein or an enzyme, abundant around a specific disease site is used as a capture molecule, the disease can be specifically detected. For the particles according to this embodiment, even when the particles do not have a capture molecule, it is possible to detect a tumor by the EPR effect.

EXAMPLES

While specific reagents and reaction conditions used in the production of the particle according to an embodiment of the present invention are described in examples, these reagents and reaction conditions may be changed, and such changes are included in the scope of the present invention. The following examples are described in order to facilitate the understanding of the present invention and are not limited to the scope of the present invention.

Method for Measuring Molar Extinction Coefficient of Particle

In the examples described below, the molar extinction coefficient of particles is measured as described below. First, a particle concentration c is determined. A particle solution having a certain volume is freeze-dried to determine the weight of the particles. The particle concentration can be calculated from the weight of the particles, the average molecular weight of the particles, and the volume of the solution before drying. Subsequently, the particle solution whose concentration has been determined is placed in an absorption cell with a width l. The cell is irradiated to light having at least one wavelength selected from a range of 600 nm to 1300 nm to determine an absorbance A at the wavelength. In the examples described below, UV/VIS Spectrometer Lambda Bio 40 (manufactured by PerkinElmer Inc.) was used as an apparatus configured to absorbance. However, any common ultraviolet and visible spectrophotometer may be used. For example, Gene Quant 1300 (manufactured by PerkinElmer Inc.) or RAMBDA 25 (manufactured by PerkinElmer Inc.) may be used.

In the case where the absorbance A exceeds 1, the particle solution is appropriately diluted. Finally, A, c, and l are substituted into the Lambert-Beer equation to determine a molar extinction coefficient $\epsilon$. in the case where l is fixed, particle solutions with several concentrations are used to check the linearity of A with respect to c.

Method for Evaluating Rate of Dye Leakage

A method for evaluating the rate of dye leakage according to this embodiment is a method that includes mixing particles prepared in each of the examples described below with a serum, heating the resulting mixture of the particles and the serum, centrifuging the mixture, recovering supernatants of the mixture before and after the centrifugation, and measuring absorbance.

The method for evaluating the rate of dye leakage will be specifically described below. The particles prepared in each of the examples are mixed with serum in a volume ratio of 1:9. The mixture is allowed to stand at 37° C. for 24 hours. As the serum, fetal bovine serum was used. However, mouse serum or the like may be used.

The mixture of the particles and the serum after standing for 24 hours is centrifuged at 80,000 rpm (288,000×g) for 17 minutes at 25° C. As a centrifuge, himac CS150GXL (manufactured by Hitachi Koki Co., Ltd.) was used.

Next, a recovery operation was performed. Specifically, 200 μL of a supernatant was carefully recovered from the mixture after centrifugation without dispersing precipitates and transferred to wells of a 96-well plate. Furthermore, 200 μL of the solution was also recovered from the mixture before centrifugation and transferred to wells different from the foregoing wells of the 96-well plate. After the completion of the recovery operation, the absorbance of the samples in the 96-well plate was measured. The leakage rate of the dye from the particles was defined as the absorbance of the supernatant after centrifugation with respect to the absorbance of the solution before centrifugation and was calculated. Furthermore, the residual rate of the dye in the particles can be determined by subtracting the rate of dye leakage from 100%. As a spectrophotometer, Varioskan (manufactured by Thermo Electron Corporation) was used. Instead of the 96-well plate, cuvettes may be used to measure the absorbance. As a spectrophotometer using a cuvette, GeneQuant 1300 (manufactured by GE Healthcare) was used. Alternatively, UV/VIS Spectrometer Lambda Bio 40 (manufactured by PerkinElmer Inc.) may be used.

Method for Measuring Photoacoustic Signal Intensity

An acoustic wave, specifically, photoacoustic signal intensity, was measured by irradiating a sample dispersed in PBS with pulsed laser light, detecting the intensity of a photoacoustic signal generated from the sample with a piezoelectric element, amplifying the signal with a high-speed preamplifier, and acquiring data with a digital oscilloscope. Specific conditions are described below. As a light source, a titanium-sapphire laser (LT-2211-PC, manufactured by Lotis Ltd.) was used. The wavelength was variable within the range of 700 to 1000 nm. At the time of measurement, a wavelength near the absorption maximum of the sample was selected. The energy density was in the range of about 10 to 20 mJ/cm$^2$. The pulse width was about 20 nanoseconds. The pulse repetition frequency was 10 Hz. As the piezoelectric element to detect the photoacoustic signal, an unfocused ultrasonic transducer (V303, manufactured by Panametrics-NDT) having an element diameter of 1.27 cm and a center frequency of 1 MHz was used. As a measuring vessel, a polystyrene cuvette having an optical path length of 0.1 cm was used. The sample volume was about 200 μL. The measuring vessel and the piezoelectric element were immersed in a glass vessel filled with water. The spacing between the measuring vessel and the piezoelectric element was 2.5 cm. As the high-speed preamplifier to amplify the photoacoustic signal intensity, an ultrasonic preamplifier having a gain of +30 dB (Model 5682, manufactured by Olympus Corporation) was used. An amplified signal was fed into a digital oscilloscope (DPO4104, manufactured by TFF Corporation). The polystyrene cuvette was irradiated with pulsed laser light from the outside of the glass vessel. Part of scattered light generated in this irradiation was detected with a photodiode and fed into the digital oscilloscope as a trigger signal. The digital oscilloscope was set to a 32 run-averaging display mode to obtain an average photoacoustic signal of 32 laser pulse irradiations. The average photoacoustic signal intensity was measured. In the case of measuring the photoacoustic signal of the sample from a living body into which the sample has been administered, the foregoing system was basically used. In the case where a small animal is measured, a heating type operation stage configured to hold the small animal and a CCD camera configured to photograph an image-pickup position were installed in addition to the foregoing system.

Example 1

Particles Containing Compound 1 (Particles 1)

Preparation of Particles 1 (PNP1)

Compound 1 described above (0.88 mg, manufactured by Sigma-Aldrich Japan K.K.) and PLGA (5 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 1.

An aqueous solution (20 mL) of Tween 20 (180 mg, manufactured by Tokyo Chemical Industry Co., Ltd.) dissolved therein was stirred at room temperature for 20 minutes or more. The dye-chloroform solution 1 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles 1 containing compound 1 in PLGA, each of particles 1 having a surface protected with Tween 20. Hereinafter, particles 1 are referred to as "PNP1".

Evaluation of Physical Properties of PNP1

Analysis of PNP1 with a dynamic light scattering spectrophotometer (DLS-8000, manufactured by Otsuka Electronics Co., Ltd) demonstrated that PNP1 had an average particle size of 125.8 nm (which is a value determined by a cumulant analysis). PNP1 had a molar extinction coefficient of $8.1 \times 10^9$ $M^{-1}$ $cm^{-1}$. The photoacoustic signal intensity was $2.3 \times 10^{11}$ $VJ^{-1}M^{-1}$.

PNP1 was subjected to the dye leakage test. The residual rate of the dye in the particles was 96%.

Example 2

Particle Containing Compound 1 (Particle 2)

Preparation of Particle 2 (PNP2)

Particles 2 (hereinafter, referred to as "PNP2") were prepared by the same method as the method for preparing PNP1, except that the amount of Tween 20 was changed from 180 mg to 90 mg.

Evaluation of Physical Properties of PNP2

Analysis of PNP2 with a dynamic light scattering spectrophotometer demonstrated that PNP2 had an average particle size of 173.7 nm (which is a value determined by a cumulant analysis). PNP2 had a molar extinction coefficient of $5.6 \times 10^{10}$ $M^{-1}$ $cm^{-1}$. The photoacoustic signal intensity was $1.7 \times 10^{12}$ $VJ^{-1}M^{-1}$. PNP2 was subjected to the dye leakage test. The residual rate of the dye in the particles was 98%.

Example 3

Particle Containing Compound 1 (Particle 3)

Preparation of Particle 3 (PNP3)

Particles 3 (hereinafter, referred to as "PNP3") were prepared by the same method as the method for preparing PNP1, except that the amount of Tween 20 was changed from 180 mg to 360 mg.

Evaluation of Physical Properties of PNP3

Analysis of PNP3 with a dynamic light scattering spectrophotometer demonstrated that PNP3 had an average particle size of 143.4 nm (which is a value determined by a cumulant analysis). PNP3 had a molar extinction coefficient of $2.8 \times 10^{10}$ $M^{-1}$ $cm^{-1}$. The photoacoustic signal intensity was $8.8 \times 10^{11}$ $VJ^{-1}M^{-1}$. PNP3 was subjected to the dye leakage test. The residual rate of the dye in the particles was 99% or more.

Example 4

Particle Containing Compound 1 (Particle 4)

Preparation of Particle 4 (PNP4)

Particles 4 (hereinafter, referred to as "PNP4") were prepared by the same method as the method for preparing PNP1, except that the amount of compound 1 was changed from 0.88 mg to 4.4 mg and that the amount of Tween 20 was changed from 180 mg to 90 mg.

Evaluation of Physical Properties of PNP4

Analysis of PNP4 with a dynamic light scattering spectrophotometer demonstrated that PNP4 had an average particle size of 180.4 nm (which is a value determined by a cumulant analysis). PNP4 had a molar extinction coefficient of $7.7 \times 10^{10}$ $M^{-1}$ $cm^{-1}$. The photoacoustic signal intensity was $2.4 \times 10^{12}$ $VJ^{-1}M^{-1}$. PNP4 was subjected to the dye leakage test. The residual rate of the dye in the particles was 99%.

Example 5

Particle Containing Compound 1 (Particle 5)

Preparation of Particle 5 (PNP5)

Particles 5 (hereinafter, referred to as "PNP5") were prepared in the same way as the method for preparing PNP1, except that the amount of compound 1 was changed from 0.88 mg to 4.4 mg.

Evaluation of Physical Properties of PNP5

Analysis of PNP5 with a dynamic light scattering spectrophotometer demonstrated that PNP5 had an average particle size of 162.1 nm (which is a value determined by a cumulant analysis). PNP5 had a molar extinction coefficient of $9.9 \times 10^{10}$ $M^{-1}$ $cm^{-1}$. The photoacoustic signal intensity was $3.0 \times 10^{12}$ $VJ^{-1}M^{-1}$. PNP5 was subjected to the dye leakage test. The residual rate of the dye in the particles was 99% or more.

Example 6

Particle Containing Compound 1 (Particle 6)

Preparation of Particle 6 (PNP6)

Particles 6 (hereinafter, referred to as "PNP6") were prepared in the same way as the method for preparing PNP1, except that the amount of compound 1 was changed from 0.88 mg to 4.4 mg and that the amount of Tween 20 was changed from 180 mg to 360 mg.

Evaluation of Physical Properties of PNP6

Analysis of PNP6 with a dynamic light scattering spectrophotometer demonstrated that PNP6 had an average particle size of 127.5 nm (which is a value determined by a cumulant analysis). PNP6 had a molar extinction coefficient of $5.2 \times 10^{10}$ $M^{-1}$ $cm^{-1}$. The photoacoustic signal intensity was $1.6 \times 10^{12}$ $VJ^{-1}M^{-1}$. PNP6 was subjected to the dye leakage test. The residual rate of the dye in the particles was 99% or more.

Example 7

Particle Containing Compound 1 (Particle 7)

Preparation of Particle 7 (PNP7)

Particles 7 (hereinafter, referred to as "PNP7") were prepared in the same way as the method for preparing PNP1, except that the amount of compound 1 was changed from 0.88 mg to 17.6 mg and that the amount of Tween 20 was changed from 180 mg to 90 mg.

Evaluation of Physical Properties of PNP7

Analysis of PNP7 with a dynamic light scattering spectrophotometer demonstrated that PNP7 had an average particle size of 137.6 nm (which is a value determined by a cumulant analysis). PNP7 had a molar extinction coefficient of $3.4 \times 10^{10}$ $M^{-1}$ $cm^{-1}$. The photoacoustic signal intensity was $1.2 \times 10^{12}$ $VJ^{-1}M^{-1}$. PNP7 was subjected to the dye leakage test. The residual rate of the dye in the particles was 99% or more.

Example 8

Particle Containing Compound 1 (Particle 8)

Preparation of Particle 8 (PNP8)

Particles 8 (hereinafter, referred to as "PNP8") were prepared in the same way as the method for preparing PNP1, except that the amount of compound 1 was changed from 0.88 mg to 17.6 mg.

Evaluation of Physical Properties of PNP8

Analysis of PNP8 with a dynamic light scattering spectrophotometer demonstrated that PNP8 had an average particle size of 116.7 nm (which is a value determined by a cumulant analysis). PNP8 had a molar extinction coefficient of $1.0 \times 10^{11}$ $M^{1}$ $cm^{-1}$. The photoacoustic signal intensity was $3.1 \times 10^{12}$ $VJ^{-1}M^{-1}$. PNP8 was subjected to the dye leakage test. The residual rate of the dye in the particles was 99% or more.

Example 9

Particle Containing Compound 1 (Particle 9)

Preparation of Particle 9 (PNP9)

Particles 9 (hereinafter, referred to as "PNP9") were prepared in the same way as the method for preparing PNP1, except that the amount of compound 1 was changed from 0.88 mg to 17.6 mg and that the amount of Tween 20 was changed from 180 mg to 360 mg.

Evaluation of Physical Properties of PNP9

Analysis of PNP9 with a dynamic light scattering spectrophotometer demonstrated that PNP9 had an average particle size of 114.4 nm (which is a value determined by a cumulant analysis). PNP9 had a molar extinction coefficient of $6.0 \times 10^{10}$ $M^{-1}$ $cm^{-1}$. The photoacoustic signal intensity was $1.5 \times 10^{12}$ $VJ^{-1}M^{-1}$. PNP9 was subjected to the dye leakage test. The residual rate of the dye in the particles was 99% or more.

Example 10

Particle Containing Compound 1 (Particle 10)

Preparation of Particle 10 (PNP10)

Compound 1 described above (4.4 mg, manufactured by Sigma-Aldrich Japan K.K.) and PLGA (5 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 2.

An aqueous solution (20 mL) of Tween 20 (180 mg, manufactured by Tokyo Chemical Industry Co., Ltd.) and SUNBRIGHT (registered trademark) DSPE-020PA (22 mg, manufactured by NOF CORPORATION, hereinafter, also referred to as "DA"), which is a phospholipid represented by chemical formula 7, dissolved therein was stirred at room temperature for 20 minutes or more. Dye-chloroform solution 2 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles 10 containing compound 1 in PLGA, each of particles 10 having a surface protected with Tween 20 and the phospholipid. Hereinafter, particles 10 are referred to as "PNP10".

Evaluation of Physical Properties of PNP10

Analysis of PNP10 with a dynamic light scattering spectrophotometer demonstrated that PNP10 had an average particle size of 168.5 nm (which is a value determined by a cumulant analysis). PNP10 had a molar extinction coefficient of $5.7 \times 10^{10}$ $M^{-1}$ $cm^{-1}$. The photoacoustic signal intensity was $2.0 \times 10^{12}$ VJ$^{-1}$M$^{-1}$. PNP10 was subjected to the dye leakage test. The residual rate of the dye in the particles was 99%.

Example 11

Particle Containing Compound 1 (Particle 11)

Preparation of Particle 11 (PNP11)

Particles 11 (hereinafter, referred to as "PNP11") were prepared in the same way as the method for preparing PNP10, except that the amount of DA was changed from 22 mg to 11 mg.
Evaluation of Physical Properties of PNP11

Analysis of PNP11 with a dynamic light scattering spectrophotometer demonstrated that PNP11 had an average particle size of 169.1 nm (which is a value determined by a cumulant analysis). PNP11 had a molar extinction coefficient of $7.8 \times 10^{10}$ M$^{-1}$ cm$^{-1}$. The photoacoustic signal intensity was $2.5 \times 10^{12}$ VJ$^{-1}$M$^{-1}$. PNP11 was subjected to the dye leakage test. The residual rate of the dye in the particles was 99% or more.

Example 12

Particle Containing Compound 1 (Particle 12)

Preparation of Particle 12 (PNP12)

Compound 1 described above (4.4 mg, manufactured by Sigma-Aldrich Japan K.K.) and PLGA (5 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 2.

An aqueous solution (20 mL) of Tween 20 (180 mg, manufactured by Tokyo Chemical Industry Co., Ltd.), SUNBRIGHT (registered trademark) DSPE-020-CN (20 mg, manufactured by NOF CORPORATION, hereinafter, also referred to as "DO"), which is a phospholipid represented by chemical formula 6, and DA (2 mg, manufactured by NOF CORPORATION) dissolved therein was stirred at room temperature for 20 minutes or more. Dye-chloroform solution 2 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles 12 containing compound 1 in PLGA, each of particles 12 having a surface protected with Tween 20 and the phospholipids. Hereinafter, particles 12 are referred to as "PNP12".
Evaluation of Physical Properties of PNP12

Analysis of PNP12 with a dynamic light scattering spectrophotometer demonstrated that PNP12 had an average particle size of 97.8 nm (which is a value determined by a cumulant analysis). PNP12 had a molar extinction coefficient of $2.0 \times 10^{10}$ M$^{-1}$ cm$^{-1}$. The photoacoustic signal intensity was $6.1 \times 10^{11}$ VJ$^{-1}$M$^{-1}$. PNP12 was subjected to the dye leakage test. The residual rate of the dye in the particles was 80%.

Example 13

Particle Containing Compound 1 (Particle 13)

Preparation of Particle 13 (PNP13)

Particles 13 (hereinafter, referred to as "PNP13") were prepared in the same way as the method for preparing PNP12, except that the amount of compound 1 was changed from 4.4 mg to 8.8 mg.
Evaluation of Physical Properties of PNP13

Analysis of PNP13 with a dynamic light scattering spectrophotometer demonstrated that PNP13 had an average particle size of 74.2 nm (which is a value determined by a cumulant analysis). PNP13 had a molar extinction coefficient of $1.2 \times 10^{10}$ M$^{-1}$ cm$^{-1}$. The photoacoustic signal intensity was $8.0 \times 10^{11}$ VJ$^{-1}$M$^{-1}$. PNP13 was subjected to the dye leakage test. The residual rate of the dye in the particles was 85%.

Example 14

Particle Containing Compound 1 (Particle 14)

Preparation of Particle 14 (PNP14)

Particles 14 (hereinafter, referred to as "PNP14") were prepared in the same way as the method for preparing PNP12, except that the amount of compound 1 was changed from 4.4 mg to 17.6 mg.
Evaluation of Physical Properties of PNP14

Analysis of PNP14 with a dynamic light scattering spectrophotometer demonstrated that PNP14 had an average particle size of 87.8 nm (which is a value determined by a cumulant analysis). PNP14 had a molar extinction coefficient of $2.7 \times 10^{10}$ M$^{-1}$ cm$^{-1}$. The photoacoustic signal intensity was $1.1 \times 10^{12}$ VJ$^{-1}$M$^{-1}$. PNP14 was subjected to the dye leakage test. The residual rate of the dye in the particles was 91%.

Example 15

Particle Containing Compound 1 (Particle 15)

Preparation of Particle 15 (PNP15)

Compound 1 described above (4.4 mg, manufactured by Sigma-Aldrich Japan K.K.) and PLGA (5 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 2.

An aqueous solution (20 mL) of Tween 20 (180 mg, manufactured by Tokyo Chemical Industry Co., Ltd.), DO (18 mg, manufactured by NOF CORPORATION), and DA (4 mg, manufactured by NOF CORPORATION) dissolved therein was stirred at room temperature for 20 minutes or more. Dye-chloroform solution 2 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles 15 containing compound 1 in PLGA, each of particles 15 having a surface protected with Tween 20 and the phospholipids. Hereinafter, particles 15 are referred to as "PNP15".
Evaluation of Physical Properties of PNP15

Analysis of PNP15 with a dynamic light scattering spectrophotometer demonstrated that PNP15 had an average particle size of 80.3 nm (which is a value determined by a cumulant analysis). PNP15 had a molar extinction coefficient of $1.0 \times 10^{10}$ $M^{-1}$ $cm^{-1}$. The photoacoustic signal intensity was $5.8 \times 10^{11}$ $VJ^{-1}M^{-1}$. PNP15 was subjected to the dye leakage test. The residual rate of the dye in the particles was 74%.

Example 16

Particle Containing Compound 1 (Particle 16)

Preparation of Particle 16 (PNP16)

Particles 16 (hereinafter, referred to as "PNP16") were prepared in the same way as the method for preparing PNP15, except that the amount of compound 1 was changed from 4.4 mg to 8.8 mg.
Evaluation of Physical Properties of PNP16

Analysis of PNP16 with a dynamic light scattering spectrophotometer demonstrated that PNP16 had an average particle size of 94.6 nm (which is a value determined by a cumulant analysis). PNP16 had a molar extinction coefficient of $2.1 \times 10^{10}$ $M^{-1}$ $cm^{-1}$. The photoacoustic signal intensity was $7.5 \times 10^{11}$ $VJ^{-1}M^{-1}$. PNP16 was subjected to the dye leakage test. The residual rate of the dye in the particles was 89%.

Example 17

Particle Containing Compound 1 (Particle 17)

Preparation of Particle 17 (PNP17)

Particles 17 (hereinafter, referred to as "PNP17") were prepared in the same way as the method for preparing PNP15, except that the amount of compound 1 was changed from 4.4 mg to 17.6 mg.
Evaluation of Physical Properties of PNP17

Analysis of PNP17 with a dynamic light scattering spectrophotometer demonstrated that PNP17 had an average particle size of 92.9 nm (which is a value determined by a cumulant analysis). PNP17 had a molar extinction coefficient of $2.7 \times 10^{10}$ $M^{-1}$ $cm^{-1}$. The photoacoustic signal intensity was $9.7 \times 10^{11}$ $VJ^{-1}M^{-1}$. PNP17 was subjected to the dye leakage test. The residual rate of the dye in the particles was 93%.

Example 18

Particle Containing Compound 1 (Particle 18)

Preparation of Particle 18 (PNP18)

Compound 1 described above (4.4 mg, manufactured by Sigma-Aldrich Japan K.K.) and PLGA (5 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 2.

An aqueous solution (20 mL) of Tween 20 (180 mg, manufactured by Tokyo Chemical Industry Co., Ltd.), DO (11 mg, manufactured by NOF CORPORATION), and DA (11 mg manufactured by NOF CORPORATION) dissolved therein was stirred at room temperature for 20 minutes or more.

Dye-chloroform solution 2 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles 18 containing compound 1 in PLGA, each of particles 18 having a surface protected with Tween 20 and the phospholipids. Hereinafter, particles 18 are referred to as "PNP18".
Evaluation of Physical Properties of PNP18

Analysis of PNP18 with a dynamic light scattering spectrophotometer demonstrated that PNP18 had an average particle size of 97.1 nm (which is a value determined by a cumulant analysis). PNP18 had a molar extinction coefficient of $1.5 \times 10^{10}$ $M^{-1}cm^{-1}$. The photoacoustic signal intensity was $5.1 \times 10^{11}$ $VJ^{-1}M^{-1}$. PNP18 was subjected to the dye leakage test. The residual rate of the dye in the particles was 86%.

Example 19

Particle Containing Compound 1 (Particle 19)

Preparation of Particle 19 (PNP19)

Particles 19 (hereinafter, referred to as "PNP19") were prepared in the same way as the method for preparing PNP18, except that the amount of compound 1 was changed from 4.4 mg to 8.8 mg.
Evaluation of Physical Properties of PNP19

Analysis of PNP19 with a dynamic light scattering spectrophotometer demonstrated that PNP19 had an average particle size of 98.3 nm (which is a value determined by a cumulant analysis). PNP19 had a molar extinction coefficient of $2.2 \times 10^{10}$ $M^{-1}$ $cm^{-1}$. The photoacoustic signal intensity was $9.6 \times 10^{11}$ $VJ^{-1}M^{-1}$. PNP19 was subjected to the dye leakage test. The residual rate of the dye in the particles was 89%.

Example 20

Particle Containing Compound 1 (Particle 20)

Preparation of Particle 20 (PNP20)

Particles 20 (hereinafter, referred to as "PNP20") were prepared in the same way as the method for preparing PNP18, except that the amount of compound 1 was changed from 4.4 mg to 17.6 mg.
Evaluation of Physical Properties of PNP20

Analysis of PNP20 with a dynamic light scattering spectrophotometer demonstrated that PNP20 had an average particle size of 105 nm (which is a value determined by a cumulant analysis). PNP20 had a molar extinction coefficient of $3.8 \times 10^{10}$ $M^{-1}$ $cm^{-1}$. The photoacoustic signal intensity was $1.1 \times 10^{11}$ $VJ^{-1}M^{-1}$. PNP20 was subjected to the dye leakage test. The residual rate of the dye in the particles was 93%.

Example 21

Particle Containing Compound 2 (Particle 21)

Preparation of Particle 21 (PNP21)

Compound 2 (4.4 mg, manufactured by Sigma-Aldrich Japan K.K.) and PLGA (20 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 3.

An aqueous solution (20 mL) of Tween 20 (60 mg, manufactured by Tokyo Chemical Industry Co., Ltd.) and DO (7.3 mg, manufactured by NOF CORPORATION) dissolved therein was stirred at room temperature for 20 minutes or more. Dye-chloroform solution 3 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles 21 containing compound 2 in PLGA, each of particles 21 having a surface protected with Tween 20 and the phospholipid. Hereinafter, particles 21 are referred to as "PNP21".

Evaluation of Physical Properties of PNP21

Analysis of PNP21 with a dynamic light scattering spectrophotometer demonstrated that PNP21 had an average particle size of 161.4 nm (which is a value determined by a cumulant analysis). PNP21 had a molar extinction coefficient of $6.7 \times 10^8$ $M^{-1}$ $cm^{-1}$. The photoacoustic signal intensity was $2.2 \times 10^{10}$ $VJ^{-1}M^{-1}$. PNP21 was subjected to the dye leakage test. The residual rate of the dye in the particles was 97%.

Example 22

Comparison of PNPs Prepared from PLGAs or Polylactic Acids Having Different Compositions or Polystyrene Preparation of Particle 22 (PNP22)

Compound 1 described above (4.4 mg, manufactured by Sigma-Aldrich Japan K.K.) and PLGA (5 mg, the composition ratio of lactic acid to glycolic acid: 50:50, average molecular weight: 20,000, manufactured by Wako Pure Chemical Industries, Ltd.) were dissolved in 1.6 mL of chloroform to prepare dye-chloroform solution 2.

Tween 20 (180 mg, manufactured by Tokyo Chemical Industry Co., Ltd.) was stirred at room temperature for 20 minutes or more. Dye-chloroform solution 2 was then added dropwise thereto under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration with an Amicon Ultra centrifugal filter unit. The centrifugal operation was performed until the absorbance at about 770 nm originating from compound 1 in the filtrate was reduced to 0.1 or less, removing an excess of the surfactant. In this way, these operations described above were performed to prepare an aqueous dispersion of particles 22 containing compound 1 in PLGA, each of particles 22 having a surface protected with Tween 20 was prepared. Hereinafter, particles 22 are referred to as "PNP22".

Evaluation of Physical Properties of PNP22

Analysis of PNP22 with a dynamic light scattering spectrophotometer demonstrated that PNP22 had an average particle size of 106.9 nm (which is a value determined by a cumulant analysis). PNP22 had a molar extinction coefficient of $1.98 \times 10^9$ $M^{-1}$ $cm^{-1}$. PNP22 was subjected to the dye leakage test. The residual rate of the dye in the particles was 69%. The results demonstrated that although the feed conditions were the same as those of PNP5 described in EXAMPLE 5, the average particle size and the residual rate of the dye in the particles were different from those of PNP5. A possible reason for this is as follows: PNP5 was subjected to centrifugal purification (20,000×g), whereas PNP22 was subjected to ultrafiltration. Thus, an excess of the surfactant was not sufficiently removed.

Preparation of PNPs from PLGAs or Polylactic Acids Having Different Compositions or Polystyrene PNPs were prepared from polymers described in Table 1 in place of PLGA used for the preparation of PNP22. Here, PLAs represent polylactic acids. PS represents polystyrene. Particles 23 to 29 (hereinafter, also referred to as "PNP23 to 29") were prepared in the same way as the method for preparing PNP22, except that different polymers were used.

TABLE 1

| Particle No. | Polymer | Average molecular weight | Lactic acid: glycolic acid | Particle size (nm) | Molar extinction coefficient ($M^{-1}$ * $cm^{-1}$) | Residual rate of dye (%) |
|---|---|---|---|---|---|---|
| PNP23 | PLGA | 50 k | 50:50 | 97.7 | 7.94E+08 | 49 |
| PNP24 | PLGA | 4-15 k | 75:25 | 107.4 | 1.43E+09 | 54 |
| PNP25 | PLGA | 66-107 k | 75:25 | 101.9 | 1.11E+09 | 47 |
| PNP26 | PLA | 20 k | 100:0 | 112.4 | 1.86E+09 | 63 |
| PNP27 | PLA | 50 k | 100:0 | 98.4 | 1.05E+09 | 52 |
| PNP28 | PLA | 100 k | 100:0 | 91.3 | 7.87E+08 | 38 |
| PNP29 | PS | 20 k | N.A. | 107.4 | 3.72E+09 | 61 |

Evaluation of Physical Properties of PNP23 to PNP29

PNP23 to PNP29 were analyzed with a dynamic light scattering spectrophotometer. PNP23 to PNP29 each had an average particle size of about 100 nm (which is a value determined by a cumulant analysis). PNP23 to PNP29 each had a molar extinction coefficient of about $8 \times 10^8$ to $2 \times 10^9$ $M^{-1}cm^{-1}$. PNP23 to PNP29 were each subjected to the dye leakage test. The residual rate of the dye in the particles was in the range of about 40% to 60%.

Figure 5:
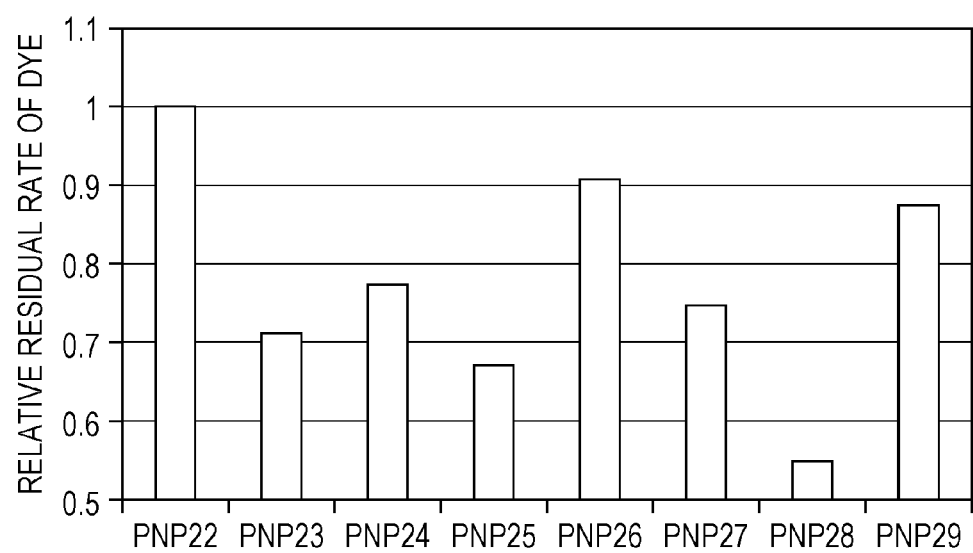
FIG. 5 is a graph illustrating the residual rate of a dye in a particle according to an example of the present invention.

PNP22 was compared with PNP23 to PNP29 in terms of the dye leakage properties. The residual dye rate of PNP22 was defined as 1. The relative residual rates of the dye in PNP23 to PNP29 were graphed (FIG. 5). The results demonstrated that PNP22 had the highest residual dye rate. FIG. 5 suggested that in order to inhibit the leakage of the dye included in the particles, the polymer may have an average molecular weight of about 20,000 and that PLGA in which the composition ratio of lactic acid to glycolic acid is 50:50 may be used, as compared with the polymers having similar molecular weights.

Comparative Example 1

Comparison with PNP Including ICG as Dye

Preparation of Particle (ICG-PNP)

Indocyanine green (hereinafter, referred to as "ICG", 4.4 mg, available from Pharmaceutical and Medical Device Regulatory Science of Japan) was dissolved in 1 mL of methanol. The resulting ICG solution was mixed with 1 mL of chloroform containing PLGA (20 mg, the composition ratio of lactic acid to glycolic acid was 50:50, average molecular weight: 20,000, manufactured by Wako Pure Chemical Industries, Ltd.) dissolved therein to prepare an ICG-methanol-chloroform solution.

An aqueous solution (20 mL) of Tween 20 (60 mg, manufactured by Tokyo Chemical Industry Co., Ltd.) and DO (7.3 mg, manufactured by NOF CORPORATION) dissolved therein was stirred at room temperature for 20 minutes or more. The ICG-methanol-chloroform solution was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles containing ICG in PLGA, each of the particles having a surface protected with Tween 20 and DO. Hereinafter, the particles are referred to as "ICG-PNP".

Evaluation of Physical Properties of ICG-PNP

Analysis of ICG-PNP with a dynamic light scattering spectrophotometer demonstrated that ICG-PNP had an average particle size of 83.4 nm (which is a value determined by a cumulant analysis). ICG-PNP had a molar extinction coefficient of $2.8 \times 10^9$ $M^{-1}$ $cm^{-1}$. The photoacoustic signal intensity was $6.8 \times 10^{10}$ $VJ^{-1}M^{-1}$. ICG-PNP was subjected to the dye leakage test. The residual rate of the dye in the particles was 12%.

Comparative Example 2

Comparison with PNP Including PMMA

Preparation of Particle (PNP-PMMA1)

Compound 1 described above (0.88 mg, manufactured by Sigma-Aldrich Japan K.K.) and poly(methyl methacrylate-co-methacrylic acid) (hereinafter, referred to as "PMMA1", 5 mg, methyl methacrylate:methacrylic acid=1:0.016, average molecular weight: 15,000, manufactured by Sigma-Aldrich Japan K.K.) were dissolved in 1.6 mL of chloroform to prepare dye-chloroform solution 4.

An aqueous solution of Tween 20 (180 mg, manufactured by Tokyo Chemical Industry Co., Ltd.) was stirred at room temperature for 20 minutes or more. Dye-chloroform solution 4 was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles containing compound 1 in PMMA1, each of the particles having a surface protected with Tween 20. Hereinafter, the particles are referred to as "PNP-PMMA1".

Preparation of Particles (PNP-PMMA2 and PNP-PMMA3)

PNPs were prepared using polymers described in Table 2 in the same way as PNP-PMMA1. In Table 2, PMMA2 represents poly(methyl methacrylate-co-butyl methacrylate) (methyl methacrylate:butyl methacrylate=85:15, average molecular weight: 75,000, manufactured by Sigma-Aldrich). PMMA3 represents poly(methyl methacrylate), isotactic (>80% isotactic, manufactured by Sigma-Aldrich). PNP including PMMA2 is referred to as "PNP-PMMA2". PNP including PMMA3 is referred to as "PNP-PMMA3"

Preparation of Particles (PNP-PMMA4, PNP-PMMA5, and PNP-PMMA6)

PNP-PMMA4, PNP-PMMA5, and PNP-PMMA6 were prepared in the same way as PNP-PMMA1 to PNP-PMMA3, except that an aqueous solution (20 mL) in which DA (11 mg, manufactured by NOF CORPORATION) was dissolved in an aqueous solution of Tween 20 was used.

TABLE 2

| Particle No. | Polymer | DA addition | Particle size (nm) | Residual rate of dye (%) |
|---|---|---|---|---|
| PNP-PMMA1 | PMMA1 | no | 138.6 | 96 |
| PNP-PMMA2 | PMMA2 | no | 132.7 | 30 |
| PNP-PMMA3 | PMMA3 | no | 136.2 | 56 |
| PNP-PMMA4 | PMMA1 | yes | 132.1 | 26 |
| PNP-PMMA5 | PMMA2 | yes | 123.1 | 24 |
| PNP-PMMA6 | PMMA3 | yes | 120.4 | 24 |

Evaluation of Physical Properties of Particles (PNP-PMMA1 to PNP-PMMA6)

PNP-PMMA1 to PNP-PMMA6 were analyzed with a dynamic light scattering spectrophotometer. PNP-PMMA1 to PNP-PMMA6 each had an average particle size of about 120 to 130 nm (which is a value determined by a cumulant analysis). PNP-PMMA1 to PNP-PMMA6 were each subjected to the dye leakage test. PNP-PMMA1 had the highest residual rate of the dye in the particles of these samples. The residual dye rate of PNP-PMMA1 was 96%, which was about 4% lower than that of PNP1 including PLGA as a polymer. In each of PNP-PMMA4 to PNP-PMMA6, which contained DA as a phospholipid, it was found that the residual dye rate was about 50% lower than that of PNP including PLGA as a polymer. Accordingly, it was found that by using PLGA as a polymer enables, it is possible to produce PNP having the highest residual dye rate.

Comparative Example 3

Comparison with Nc-PNP

First, 2,3-naphthalocyanine (4.4 mg, manufactured by Sigma-Aldrich Japan K.K.) and PLGA (20 mg, the composition ratio of lactic acid to glycolic acid: 50:50, average molecular weight: 20,000, manufactured by Wako Pure Chemical Industries, Ltd.) were dissolved in 1.6 mL of chloroform to prepare a chloroform solution of 2,3-naphthalocyanine.

An aqueous solution (20 mL) of Tween 20 (60 mg, manufactured by Tokyo Chemical Industry Co., Ltd.) and DO (7.3 mg, manufactured by NOF CORPORATION) dissolved therein was stirred at room temperature for 20 minutes or more. The chloroform solution of 2,3-naphthalocyanine was then added dropwise to the aqueous solution under stirring. The resulting mixed solution was stirred for 30 minutes. The mixed solution was treated with an ultrasonic dispersion machine 90 seconds to prepare an O/W emulsion.

The emulsion was stirred under heating (40° C.) to remove chloroform from the dispersoids. Then the emulsion was subjected to ultrafiltration or centrifugation to remove an excess of the surfactant, thereby preparing an aqueous dispersion of particles containing 2,3-naphthalocyanine in PLGA, each of the particles having a surface protected with Tween 20 and the phospholipid. Hereinafter, the particles are referred to as "Nc-PNP".

Evaluation of Physical Properties of Nc-PNP

The average particle size of Nc-PNP was analyzed with a dynamic light scattering spectrophotometer and found to be 162.6 nm (which is a value determined by a cumulant analysis). Nc-PNP had a molar extinction coefficient of $6.7 \times 10^8$ $M^{-1}cm^{-1}$. Nc-PNP was subjected to the dye leakage test. The residual rate of the dye in the particles was 93%. In the case of particles prepared in the same way as Nc-PNP and using compound 1 in place of 2,3-naphthalocyanine, the average particle size was 166.3 nm (which is a value determined by a cumulant analysis). The molar extinction coefficient was $1.6 \times 10^{11}$ $M^{-1}cm^{-1}$. The residual rate of the dye in the particles was 92%. A comparison of the particles using compound 1 with Nc-PNP demonstrated that while there was no significant difference in residual dye rate, there was a large difference in molar extinction coefficient, and the molar extinction coefficient of the particles using compound 1 was 150 times that of Nc-PNP. This is because of a difference in the amount of the dye included in the particles. In fact, in the case of the particles using compound 1, 84% of the amount of compound 1 fed to the system was present in the particles. In contrast, in the case of Nc-PNP, only 11% of the amount of 2,3-naphthalocyanine fed was present. Accordingly, in order to produce particles having a high residual rate of the dye in the particles and a high molar extinction coefficient, it is probably effective in using a naphthalocyanine dye including Si as a central metal, for example, a naphthalocyanine dye including Si, which serves as a central metal, bound to a bulky molecule, such as an alkyl chain.

Example 23

Tumor Imaging Using Particle 10 (PNP10)

In tumor imaging, female outbred BALB/c Slc-nu/nu mice (6 weeks old on purchase) (Japan SLC Inc.) were used. The mice were acclimated using standard feeds and beddings and given food and drinking water ad libitum for 1 week before cancer cells were transplanted. At approximately 2 weeks before an imaging experiment, $2 \times 10^6$ N87 human gastric cancer cells (ATCC#CRL-5822) were subcutaneously injected into the left shoulder of each mouse. Tumor cells had been all established by the time of the experiment. The body weights of the mice were between 17 and 22 g. Then 200 µL (13 nmol in terms of particles) of PBS solutions of PNP10 were intravenously injected into the tumor-bearing mice.

As a first comparative example, an aqueous dispersion of particles was prepared as in EXAMPLE 10, except that polystyrene (hereinafter, also referred to as "PS") (5 mg, average molecular weight: 20,000, manufactured by Tokyo Chemical Industry Co., Ltd.) was used in place of PLGA (5 mg). Hereinafter, the particles are referred to as "PNP-PS". As a second comparative example, an aqueous solution in which compound 1 was dispersed in FBS was prepared. Hereinafter, the aqueous solution is referred to as "Dye". Then 200 µL (13 nmol in terms of the particles; for Dye, 13 nmol in terms of the amount of the dye) of PBS solutions of PNP-PS or Dye were intravenously injected into the tails of the foregoing tumor-bearing mice.

With respect to the tumor-bearing mice into which PNP10, PNP-PS, or Dye was administered, all injections were tolerated well, judging by the lack of any visible problems. A whole-body fluorescence image of each of the mice into which PNP10, PNP-PS, or Dye was administered was taken 24 hours after injection with an IVIS (registered trademark) Imaging System 200 Series (Xenogen Corporation). Furthermore, the region of a tumor site was selected from an image simultaneously captured with a CCD camera, and fluorescence intensity in the region was calculated.

Subsequently, blood was collected from each mouse 24 hours after the measurement of the whole-body fluorescence image. A method for collecting blood is described below. A tail vein different from the tail vein through which PNP10, PNP-PS, or Dye were administered was cut with a knife. Blood flowing out was collected in hematocrit tubes. Each hematocrit tube containing blood was placed in the IVIS (registered trademark of Xenogen Corporation) Imaging System 200 Series (Xenogen Corporation), and a fluorescence image was measured. Living Image (registered trademark of Xenogen Corporation) software version 2.3 with the IVIS (registered trademark of Xenogen Corporation) Imaging System 200 Series (Xenogen Corporation) was used. Equal-area observational regions (regions of interest (ROI)) were set, and fluorescence values of the hematocrit tubes were calculated. PNP10, PNP-PS, or Dye with a known concentration was diluted with mouse blood into various concentrations. The diluted samples were collected in hematocrit tubes. Each of the hematocrit tubes was placed in the IVIS (registered trademark of Xenogen Corporation) Imaging System 200 Series (Xenogen Corporation), and the fluorescence image was measured. As with the method described above, Living Image (registered trademark of Xenogen Corporation) software version 2.3 was used. Equal-area observational regions (regions of interest (ROI)) were set, and fluorescence values of the hematocrit tubes were calculated. A relational expression was derived from the calculated fluorescence values and the concentrations of PNP10, PNP-PS, or Dye. The amount of PNP10, PNP-PS, or Dye present in mouse blood was calculated on the basis of the relational expression and the fluorescence values of the hematocrit tubes containing blood collected from the tail veins of the mice. The proportion (% ID) of abundance in blood relative to the total amount administered was calculated by dividing the calculated abundance in blood by the total amount administered.

Figure 6A:
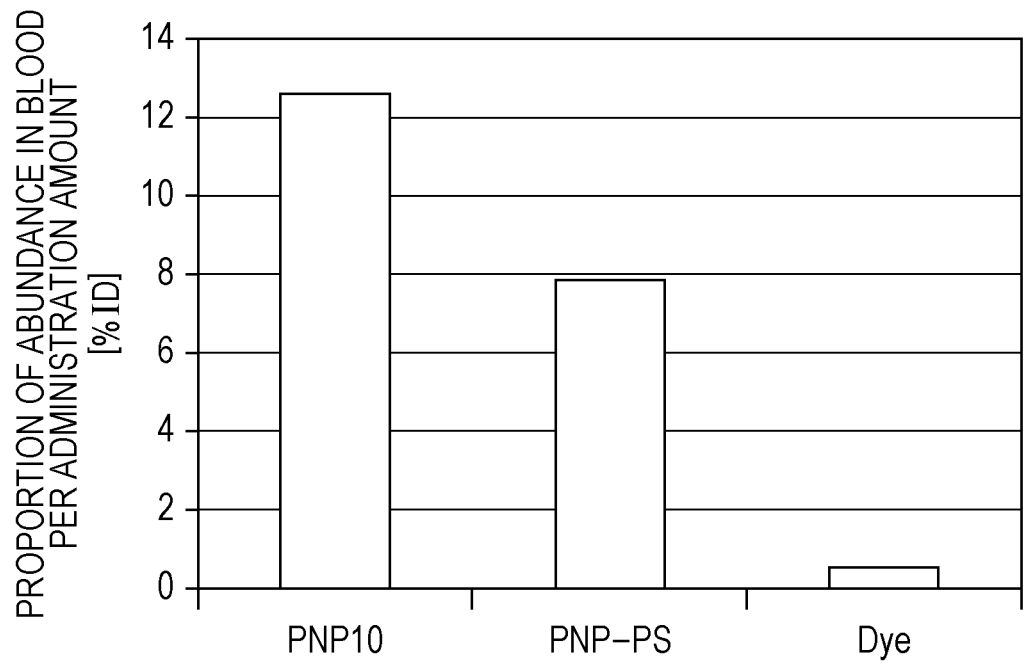
FIG. 6A is a graph illustrating the proportion of the abundance of particles in blood per amount of the particles administered according to an example of the present invention.

The calculated results were illustrated in FIG. 6A. The proportion of Dye was 0.5% ID. The proportion of PNP-PS was 7.9% ID. The proportion of PNP10 was 12.6% ID. The proportion of abundance of PNP10 in blood after 24 hours was high, compared with Dye and PNP-PS.

Then the proportion (% ID/g) of tumor accumulation relative to the total amount administered when normalized to the weight of a tumor tissue was calculated. First, PNP10, PNP-PS, or Dye with a known concentration was diluted with FBS into various concentrations, and 50 µL of the diluted samples were subcutaneously injected into mice. The fluorescence intensity at each site administered was measured with the IVIS (registered trademark of Xenogen Corporation) Imaging System 200 Series (Xenogen Corporation). Here, the amount administered, i.e., 50 µL, was determined because it was the same volume as the average size (50 mg) of N87 tumor. Next, a relational expression was derived from the fluorescence intensity at subcutaneous tissues of the mice obtained by the measurement described above and the concentrations of PNP10, PNP-PS, or Dye subcutaneously administered into the mice. The proportion of the amount of PNP10, PNP-PS, or Dye accumulated in the tumor was calculated on the basis of the relational expression and the fluorescence intensity in the region of the tumor site. Here, in the measurement of the fluorescence intensity, regions of interest of equal size were used for the subcutaneous injection and the tumor site.

Figure 6B:
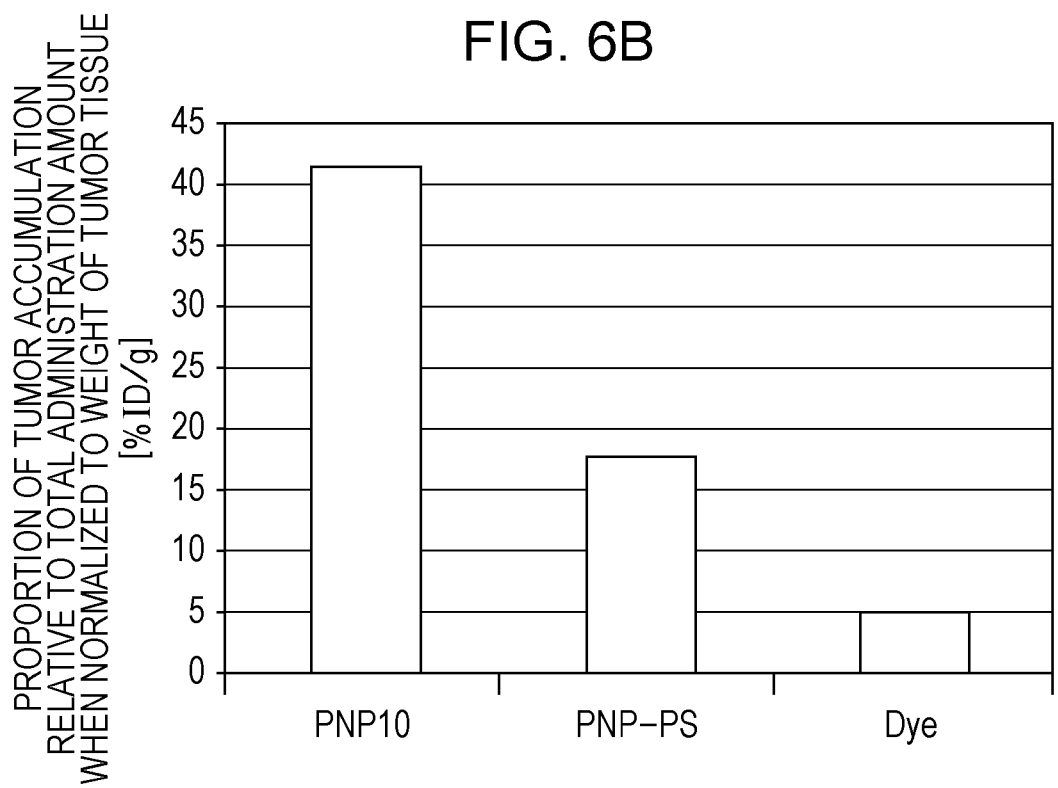
FIG. 6B is a graph illustrating the proportion of the particles accumulated in a tumor.

The calculated results were illustrated in FIG. 6B. The proportion of Dye was 4.8% ID/g. The proportion of PNP-PS was 17.7% ID/g. The proportion of PNP10 was 41.6% ID/g.

The proportion of the amount of PNP10 accumulated in the tumor after 24 hours was high, compared with Dye and PNP-PS.

Another tumor-bearing mouse into which PNP10 was administered was subjected to photoacoustic imaging. The results are illustrated in FIGS. 7A to 7C. A high-intensity photoacoustic signal (FIG. 7A) was observed at the position (FIG. 7B) of the tumor determined with the CCD camera. The same tumor-bearing mouse was subjected to fluorescence imaging (FIG. 7C). The position of a high-intensity signal was matched to the position of the high-intensity photoacoustic signal. The results demonstrated that administered PNP10 was accumulated in the tumor and generated the fluorescence and the photoacoustic signal.

Example 24

Evaluation of Physical Properties of PNPs Having Different Particle Size

PNP5 was prepared by the method described in Example 5. As a purification method, centrifugal purification (20,000×g, 45 minutes) was performed. After centrifugal purification, the resulting supernatant was recovered and further centrifuged at 72,100×g for 15 minutes. The precipitated fractions were recovered and redispersed in PBS. Hereinafter, the particles contained in the redispersed solution is referred to as "PNP5'".

Figure 8:
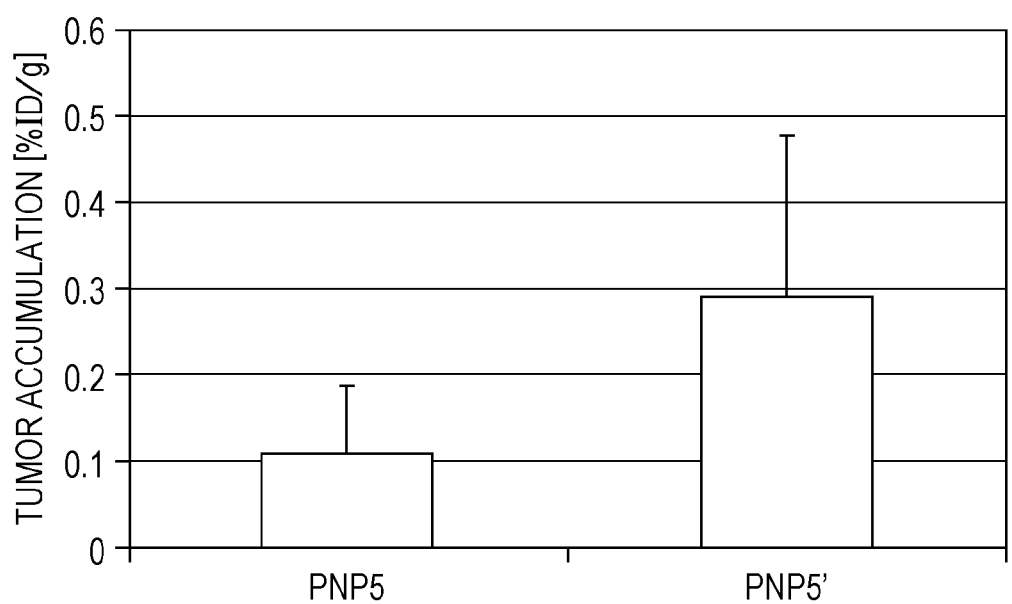
FIG. 8 is a graph illustrating the dependence of the tumor accumulation of particles according to an example of the present invention on the average particle size.

The average particle size of PNP5' was analyzed with a dynamic light scattering spectrophotometer. PNP5' had an average particle size of 49.3 nm (which is a value determined by a cumulant analysis). PNP5' had a molar extinction coefficient of $3.1 \times 10^9$ $M^{-1}cm^{-1}$. PNP5' was subjected to the dye leakage test. The residual rate of the dye in the particles was 55%. The reason for the low residual rate of the dye of PNP5' is that the particles are not sufficiently precipitated at a centrifugal force (28,800×g) during centrifugation because of its small particle size and thus are left in the supernatant.
Evaluation of Tumor Accumulation of PNP Having Different Particle Size Tumor-bearing mice were prepared in the same way as in EXAMPLE 23. Then 200 μL (13 nmol in terms of the particles) of PBS solutions of PNP5 or PNP5' were intravenously injected. With respect to the tumor-bearing mice into which PNP5 or PNP5' was administered, all injections were tolerated well, judging by the lack of any visible problems. The mice were euthanized with carbon dioxide 24 hours after administration, and the tumor tissues were extirpated. The tumor tissues were transferred to a plastic tube. An aqueous solution of 1% Triton-X100 was added thereto in an amount 1.25 times the weight of the tumor tissues. The mixture was homogenized. Then tetrahydrofuran (THF) was added thereto in an amount 20.25 times the weight of the tumor tissues. The fluorescence intensity of the homogenate solution in the plastic tube was measured with IVIS (registered trademark of Xenogen Corporation) Imaging System 200 Series (Xenogen Corporation) to quantitatively determine the amount of the dye in the tumor tissues. The results were summarized in FIG. 8. The transfer rates of PNP5 and PNP5' into the tumor tissues with respect to the amounts of PNP5 and PNP5' administered were 0.11% and 0.29% (per gram of the tumor tissues), respectively. Thus, the results demonstrated that the tumor accumulation of PNP5' having an average particle size of 49.3 nm (which is a value determined by a cumulant analysis) was greater than PNP5 having an average particle size of 162.1 nm (which is a value determined by a cumulant analysis).

Example 25

Evaluation of Accumulation Rate in Lymph Node

PNP10 prepared in EXAMPLE 10 was administered subcutaneously into the plantar surface of a mouse. Extirpation was performed 24 hours after administration. After homogenization, extraction was performed with an organic solvent to measure the accumulation rate in the popliteal lymph nodes. The amount administered was 13 nmol in terms of the amount of the dye. As a comparative example, an aqueous solution of ICG was also administered, and the accumulation rate was measured. Table 3 illustrates the results. The accumulation rate of PNP10 in the lymph nodes was about 80 times higher than that of ICG. The results demonstrated that the particles according to an embodiment of the present invention may be used for the imaging of lymph nodes.

TABLE 3

| Particle No. | Accumulation rate in lymph node (% ID) |
|---|---|
| PNP10 | 8.8 |
| ICG | 0.1 |

Photoacoustic Imaging of Lymph Node

Figure 9A:
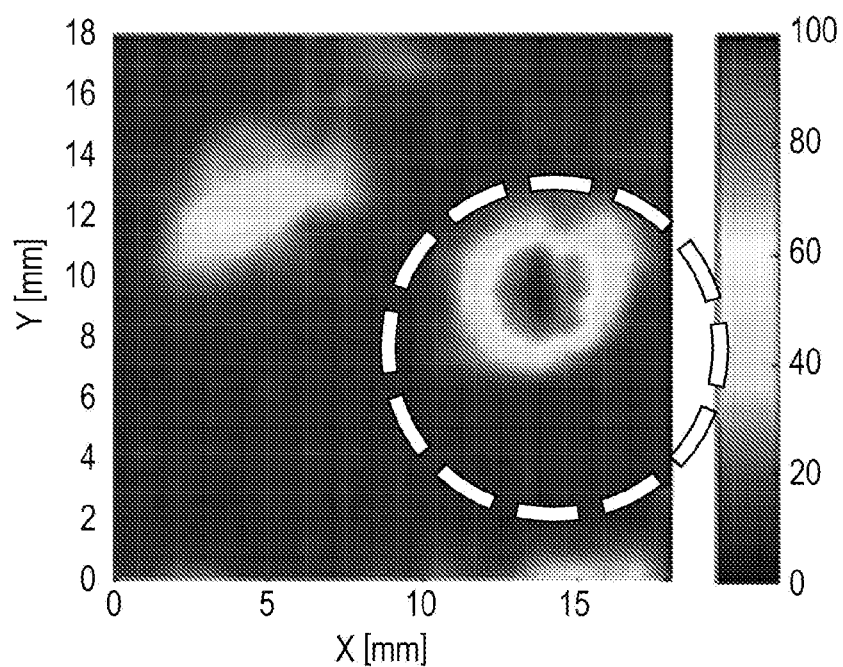
FIGS. 9A and 9B illustrate the results of the measurement of photoacoustic imaging of a mouse to which particles (PNP10) according to an example of the present invention is administered.
Figure 9B:
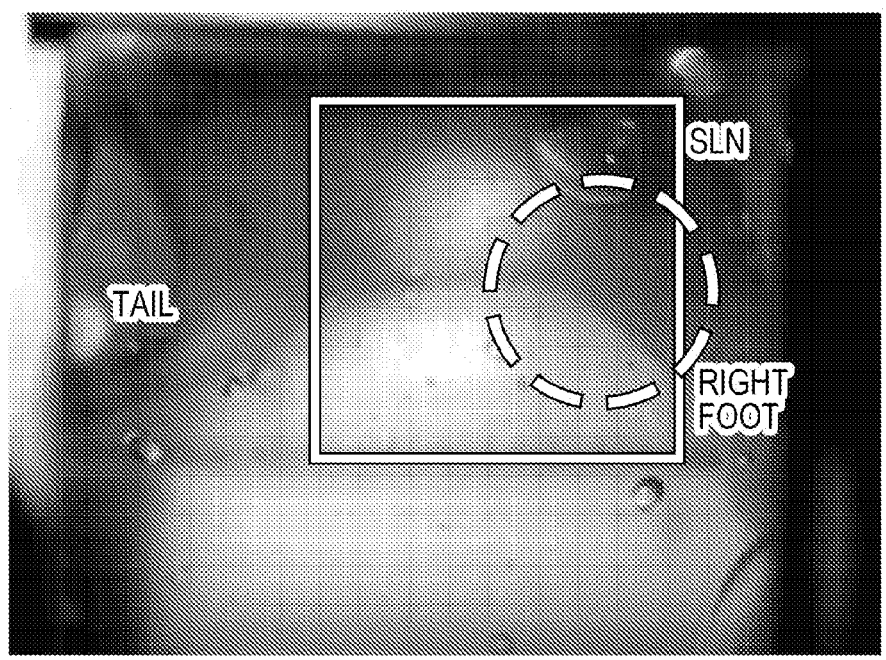

PNP10 was administered subcutaneously into the plantar surface of a mouse. The popliteal lymph node was subjected to photoacoustic imaging 24 hours after administration. The results were illustrated in FIGS. 9A and 9B. A high-intensity photoacoustic signal (FIG. 9A) was observed in the vicinity of the lymph node observed in FIG. 9B. As a comparative example, no fluorescence signal was observed from unadministered lymph nodes. The results demonstrated that the particles according to an embodiment of the present invention may function as a photoacoustic agent used for lymph node imaging.

Example 26

PNP Having Capture Molecule

Preparation of Single-Stranded Antibody hu4D5-8scFv

A gene hu4D5-8scFv coding for a single-stranded antibody (scFv) was prepared on the basis of the gene sequence (hu4D5-8) of the variable region of IgG that binds to HER2. First, cDNA was prepared by ligating the VL and VH genes of hu4D5-8 with cDNA coding for a peptide (GGGGS)3. The recognition site of a restriction enzyme NcoI was introduced at the 5' end. The recognition site of a restriction enzyme NotI was introduced at the 3' end. The nucleotide sequence is described below.

SEQ ID NO. 1:
5'-<u>CCATG</u>GATATCCAGATGACCCAGTCCCCGAGCTCCCTGTCCGCCTCT

GTGGGCGATAGGGTCACCATCACCTGCCGTGCCAGTCAGGATGTGAATAC

TGCTGTAGCCTGGTATCAACAGAAACCAGGAAAAGCTCCGAAACTACTGA

-continued
TTTACTCGGCATCCTTCCTCTACTCTGGAGTCCCTTCTCGCTTCTCTGGA

TCCAGATCTGGGACGGATTTCACTCTGACCATCAGCAGTCTGCAGCCGGA

AGACTTCGCAACTTATTACTGTCAGCAACATTATACTACTCCTCCCACGT

TCGGACAGGGTACCAAGGTGGAGATCAAAGGCGGTGGTGGCAGCGGTGGC

GGTGGCAGCGGCGGTGGCGGTAGCGAGGTTCAGCTGGTGGAGTCTGGCGG

TGGCCTGGTGCAGCCAGGGGGCTCACTCCGTTTGTCCTGTGCAGCTTCTG

GCTTCAACATTAAAGACACCTATATACACTGGGTGCGTCAGGCCCCGGGT

AAGGGCCTGGAATGGGTTGCAAGGATTTATCCTACGAATGGTTATACTAG

ATATGCCGATAGCGTCAAGGGCCGTTTCACTATAAGCGCAGACACATCCA

AAAACACAGCCTACCTGCAGATGAACAGCCTGCGTGCTGAGGACACTGCC

GTCTATTATTGTTCTAGATGGGGAGGGGACGGCTTCTATGCTATGGACTA

CTGGGGTCAAGGAACCCTGGTCACCGTCTCCTCG<u>GCGGCCGC</u>-3'

(The recognition sites of the restriction enzymes are underlined).

The foregoing gene fragment hu4D5-8scFv was inserted downstream of the T7/lac promoter of a plasmid pET-22b(+) (Novagen). Specifically, the foregoing cDNA was ligated to pET-22b(+) digested with the restriction enzymes NcoI and NotI.

This expression plasmid was transformed into *Escherichia coli* (BL21(DE3)) to obtain a bacterial strain for expression. The obtained bacterial strain was precultured overnight in 4 mL of an LB-Amp medium. The total amount was added to 250 mL of a 2xYT medium and cultured at 28° C. with shaking at 120 rpm for 8 hours. Then isopropyl-β-D(−)-thiogalactopyranoside (IPTG) was added at a final concentration of 1 mM. The bacteria were cultured overnight at 28° C. The culture broth of *Escherichia coli* were centrifuged at 8000×g for 30 minutes at 4° C. The culture broth supernatant was collected. Ammonium sulfate of 60% of the weight of the obtained culture broth was added. Proteins were precipitated by salting out. The solution subjected to salting out was allowed to stand overnight at 4° C. and centrifuged at 8000×g for 30 minutes at 4° C. to collect precipitates. The resulting precipitate were dissolved in 20 mM Tris.HCl/500 mM NaCl buffer. The mixture was dialyzed against 1 L of 20 mM Tris.HCl/500 mM NaCl buffer. After the dialysis, the protein solution was added to a column filled with His.Bind (registered trademark) Resin (Novagen) and purified by metal chelate affinity chromatography using a Ni ion. The purified hu4D5-8scFv exhibited a single band on reduced SDS-PAGE and had a molecular weight of about 28 kDa. The amino acid sequence of the prepared antibody is described below. Hereinafter, hu4D5-8scFv is referred to as "scFv".

SEQ ID NO. 2:
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASGFN

IKDTYIHWVRQAPGKGLEWVARIYPTNGYTRYADSVKGRFTISADTSKNT

AYLQMNSLRAEDTAVYYCSRWGGDGFYAMDYWGQGTLVTVSSAAALEHHH

HHHGGC

Labeling PNP10 with scFv

The buffer for scFv prepared as described above was replaced with a phosphate buffer (2.68 mM KCl/137 mM NaCl/1.47 mM $KH_2PO_4$/1 mM $Na_2HPO_4$/5 mM EDTA, pH 7.4) containing 5 mM EDTA. The solution was reduced with 10-fold molar quantity of tri(2-carboxyethyl) phosphine hydrochloride (TCEP) at 25° C. for about 2 hours.

scFv was labeled via a primary amino group present on the surface of PNP10 prepared in EXAMPLE 10. First, 0.1 mg (233 nmol) of succinimidyl-[(N-maleimidopropionamido)-diethyleneglycol]ester $(SM(PEG)_2$, Thermo Fisher Scientific K.K.) was dissolved in 2.9 mL of the aqueous dispersion (PNP concentration, $4.8 \times 10^{12}$/mL) of PNP10. Subsequently, 0.33 mL of a borate buffer (pH 8.5) was added. This particle suspension was stirred at room temperature for 2 hours. Maleimide group-introduced PNP10 (hereinafter, referred to as maleimidated PNP10) and unreacted $SM(PEG)_2$ were separated with a PD-10 desalting column (GE Healthcare Biosciences) using water as a developing solvent to obtain about 6 mL of an aqueous solution of maleimidated PNP10. Then 120 μL of a 1 M 2-[4-(2-hydroxyethyl)-1-piperazinyl]ethanesulfonic acid (HEPES) solution was added to this aqueous solution to obtain a HEPES solution of maleimidated PNP10.

The reduced scFv was added to the HEPES solution of maleimidated PNP10 and reacted at 4° C. for 15 hours or more. The reaction molar ratio (scFv/maleimidated PNP10) of the fed substances was 720. The term "fed" used herein indicates addition to a reaction system. The expression "reaction molar ratio of the fed substances" indicates a molar concentration ratio of scFv and maleimidated PNP10 added to the reaction system. After reaction, 16.8 nmol of polyethylene glycol (molecular weight: 1000, PLS-606, manufactured by Creative PEGWorks) having a thiol group at an end was added to this solution. The mixture was stirred at room temperature for 30 minutes. Subsequently, this solution was filtered with a filter (pore size: 1.2 μm). Then scFv molecules that did not bind to maleimidated PNP10 were removed by ultrafiltration with Amicon Ultra-4 (Nihon Millipore K.K.) having a pore size of 100 kDa to obtain scFv-labeled PNP10. Hereinafter, the resulting particles are referred to as "scFv-PNP10".

Evaluation of Physical Properties of scFv-PNP10

The amount of PNP10 labeled with scFv was determined using the bicinchoninic acid (BCA) method. It was found that each particle was labeled with 280 scFv molecules. The average particle size of scFv-PNP10 was analyzed with a dynamic light scattering spectrophotometer and found to be about 400 nm (which is a value determined by a cumulant analysis).

Evaluation of Ability of scFv-PNP10 to Bind to Cells

The ability of scFv-PNP10 to bind to cultured cells was evaluated. On the day before, HER2-positive cells (N87 cells) or HER2-negative cells (SUIT-2 cells) were seeded on a 48-well plate ($4 \times 10^5$ cells/well). On the following day, the medium was removed. After 200 μl, of a growth medium was placed, 100 μL of scFv-PNP10 was added in various concentrations (PNP concentrations of 0.57, 1.1, 2.3, 4.6, and 9.1 pM). The medium was allowed to stand at 4° C. for 3 hours. Then, the medium containing scFv-PNP10 was removed. The plates were washed twice with 1 mL of PBS. After PBS was removed, 300 μL of an aqueous solution of 1% Triton X-100 (polyoxyethylene-p-isooctylphenol) per well was added to lyse cells. The plates were incubated at 37° C. for 1 hour or longer. This Triton solution was transferred to a microtube. Then 200 μL of THF was added thereto. The amount of the dye in the solution was determined by fluorometry. Fluorometry was performed with an excitation wavelength of 730 nm and a fluorescence wavelength of 820 nm. A Scatchard plot was created with fluorescence intensity and the concentration of incubated scFv-PNP10. The apparent equilibrium dissociation constant (KD) of scFv-PNP10 against N87 cells was 0.35 nM. Binding to SUIT-2 cells was weak, so that the fluorescence intensity was low. Thus, KD was not determined from the Scatchard plot. These results demonstrated that scFv-PNP10 recognizes HER2 and binds selectively to HER2-positive cells.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-037576, filed Feb. 23, 2012, which is hereby incorporated by reference herein in its entirety.

What is claimed is:

1. A particle comprising:
   a copolymer of lactic acid and glycolic acid; and
   at least one compound selected from silicon naphthalocyanine and derivatives of silicon naphthalocyanine,
   wherein the particle has a particle size of 10 nm or more and less than 1000 nm,
   wherein the particle includes a capture molecule that binds specifically to a target site, and
   wherein the capture molecule is a single-stranded antibody that is represented by SEQ ID NO. 2.

2. The particle according to claim 1, wherein the compound is represented by chemical formula 3:

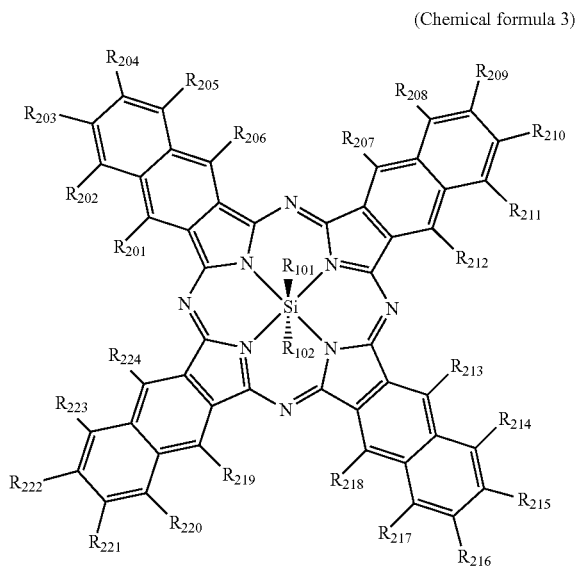

(Chemical formula 3)

wherein in chemical formula 3, $R_{201}$ to $R_{224}$ are each independently selected from a hydrogen atom, a halogen atom, an acetoxy group, an amino group, a nitro group, a cyano group, a substituted or unsubstituted alkyl group having 1 to 18 carbon atoms, and a substituted or unsubstituted aromatic group, and the substituents of the hydrocarbon group and the aromatic group each represent a halogen atom, an acetoxy group, an amino group, a nitro group, a cyano group, or an alkyl group having 1 to 18 carbon atoms;

$R_{101}$ and $R_{102}$ are each independently selected from —OH, —OR$_{11}$, —OCOR$_{12}$, —OSi(—R$_{13}$)(—R$_{14}$)(—R$_{15}$), a halogen atom, an acetoxy group, an amino group, a nitro group, a cyano group, a substituted or unsubstituted alkyl group having 1 to 18 carbon atoms, and a substituted or unsubstituted aromatic group, and the substituents of the hydrocarbon group and the aromatic group each represent a halogen atom, an acetoxy group, an amino group, a nitro group, a cyano group, or an alkyl group having 1 to 18 carbon atoms; and $R_{11}$ to $R_{15}$ are each independently selected from a hydrogen atom, a halogen atom, an acetoxy group, an amino group, a nitro group, a cyano group, a substituted or unsubstituted alkyl group having 1 to 18 carbon atoms, and a substituted or unsubstituted aromatic group, and the substituents of the hydrocarbon group and the aromatic group each represent a halogen atom, an acetoxy group, an amino group, a nitro group, a cyano group, or an alkyl group having 1 to 18 carbon atoms.

3. The particle according to claim 1, wherein the compound is a compound represented by chemical formula 1, a compound represented by chemical formula 2, silicon 2,3-naphthalocyanine dioctyloxide, silicon 2,3-naphthalocyanine dichloride, or bis(di-isobutyl octadecylsiloxy)silicon 2,3-naphthalocyanine (isoBOSINC)

(Chemical formula 1)

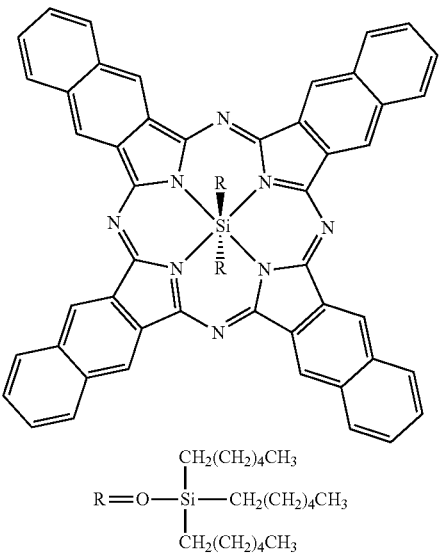

$R=O—Si(CH_2(CH_2)_4CH_3)_3$ (Chemical formula 2)

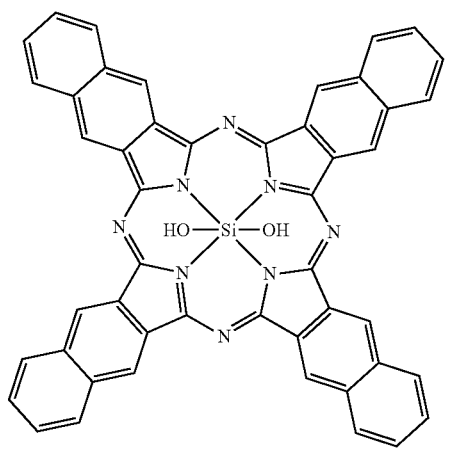

4. The particle according to claim 1, wherein in the copolymer, the copolymerization ratio of lactic acid to glycolic acid is in the range of 25:75 to 75:25.

5. The particle according to claim 1, wherein the particle includes at least one type of surfactant on a surface of the particle.

6. The particle according to claim 5, wherein the surfactant is polyoxyethylene sorbitan fatty acid esters.

7. The particle according to claim 6, wherein the polyoxyethylene sorbitan fatty acid esters are represented by chemical formula 4:

(Chemical formula 4)

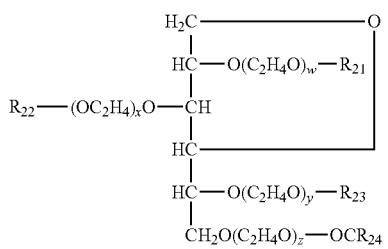

wherein in chemical formula 4, $R_{21}$ to $R_{24}$ are each independently selected from —H and —OCR', R' represents a saturated or unsaturated alkyl group having 1 to 18 carbon atoms; and the sum total of w, x, y, and z is an integer of 10 to 30.

8. A contrast agent for optical imaging, comprising:
the particles according to claim 1; and
a dispersion medium, the particles being dispersed in the dispersion medium.

9. A contrast agent for photoacoustic imaging, comprising:
the particles according to claim 1; and
a dispersion medium, the particles being dispersed in the dispersion medium.

10. The particle according to claim 5, wherein the surfactant is phospholipids.

11. The particle according to claim 1, wherein an average molecular weight of the copolymer is 15,000 or more and 25,000 or less.

* * * * *

SEQUENCE LISTING

<160> NUMBER OF SEQ ID NOS: 2

<210> SEQ ID NO 1
<211> LENGTH: 739
<212> TYPE: DNA
<213> ORGANISM: Artificial Sequence
<220> FEATURE:
<223> OTHER INFORMATION: Gene sequence coding for single-stranded antibody hu4D5-8scFv, prepared based on gene sequence hu4D5-8 of variable region of IgG that binds to HER2

<400> SEQUENCE: 1

```
ccatggatat ccagatgacc cagtccccga gctccctgtc cgcctctgtg ggcgataggg      60
tcaccatcac ctgccgtgcc agtcaggatg tgaatactgc tgtagcctgg tatcaacaga     120
aaccaggaaa agctccgaaa ctactgattt actcggcatc cttcctctac tctggagtcc     180
cttctcgctt ctctggatcc agatctggga cggatttcac tctgaccatc agcagtctgc     240
agccggaaga cttcgcaact tattactgtc agcaacatta tactactcct ccacgttcg      300 gacagggtac caaggtggag atcaaggcg gtggtggcag cggtggcggt ggcagcggcg     360
gtggcggtag cgaggttcag ctggtggagt ctggcggtgg cctggtgcag ccagggggct     420
cactccgttt gtcctgtgca gcttctggct tcaacattaa agacacctat atacactggg     480
tgcgtcaggc cccgggtaag ggcctggaat gggttgcaag gatttatcct acgaatggtt     540
atactagata tgccgatagc gtcaagggcc gtttcactat aagcgcagac acatccaaaa     600
acacagccta cctgcagatg aacagcctgc gtgctgagga cactgccgtc tattattgtt     660
ctagatgggg aggggacggc ttctatgcta tggactactg gggtcaagga accctggtca     720
ccgtctcctc ggcggccgc                                                 739
```

<210> SEQ ID NO 2
<211> LENGTH: 256
<212> TYPE: PRT
<213> ORGANISM: Artificial Sequence
<220> FEATURE:
<223> OTHER INFORMATION: Single-stranded antibody sequence hu4D5-8scFv

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

-continued

```
Thr Phe Gly Gln Gly Thr Lys Val Glu Ile Lys Gly Gly Gly Gly Ser
            100             105             110
Gly Gly Gly Gly Ser Gly Gly Gly Ser Glu Val Gln Leu Val Glu
        115             120             125
Ser Gly Gly Gly Leu Val Gln Pro Gly Gly Ser Leu Arg Leu Ser Cys
        130             135             140
Ala Ala Ser Gly Phe Asn Ile Lys Asp Thr Tyr Ile His Trp Val Arg
145                 150             155             160
Gln Ala Pro Gly Lys Gly Leu Glu Trp Val Ala Arg Ile Tyr Pro Thr
                165             170             175
Asn Gly Tyr Thr Arg Tyr Ala Asp Ser Val Lys Gly Arg Phe Thr Ile
            180             185             190
Ser Ala Asp Thr Ser Lys Asn Thr Ala Tyr Leu Gln Met Asn Ser Leu
        195             200             205
Arg Ala Glu Asp Thr Ala Val Tyr Tyr Cys Ser Arg Trp Gly Gly Asp
        210             215             220
Gly Phe Tyr Ala Met Asp Tyr Trp Gly Gln Gly Thr Leu Val Thr Val
225             230             235             240
Ser Ser Ala Ala Ala Leu Glu His His His His His His Gly Gly Cys
            245             250             255
```